(12) United States Patent
Blumenthal et al.

(10) Patent No.: US 6,705,453 B2
(45) Date of Patent: *Mar. 16, 2004

(54) METHOD AND APPARATUS UTILIZING SERVO MOTORS FOR PLACING PARTS ONTO A MOVING WEB

(75) Inventors: Jeffrey H. Blumenthal, Batavia, OH (US); Michael J. Lamping, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 403 days.

This patent is subject to a terminal disclaimer.

(21) Appl. No.: 09/897,822

(22) Filed: Jun. 29, 2001

(65) Prior Publication Data

US 2002/0023723 A1 Feb. 28, 2002

Related U.S. Application Data

(63) Continuation-in-part of application No. 09/620,867, filed on Jul. 21, 2000, now Pat. No. 6,450,321.

(51) Int. Cl.[7] .............................................. B65G 47/32
(52) U.S. Cl. ................... 198/471.1; 198/459.8; 198/408; 198/460.1; 198/461.2; 198/472.1; 156/520; 156/521; 156/552; 156/568
(58) Field of Search ...................... 198/459.8, 471.1, 198/472.1, 803.5, 803, 408, 460.1, 461.1, 461.2; 156/552, 567, 568, 519–521

(56) References Cited

U.S. PATENT DOCUMENTS

| | | | |
|---|---|---|---|
| 4,333,790 A | | 6/1982 | Schaffron |
| 4,429,781 A | * | 2/1984 | Holzhauser ................. 198/448 |
| 5,091,039 A | * | 2/1992 | Ujimoto et al. ............. 156/519 |
| 5,235,515 A | * | 8/1993 | Ungpiyakul et al. ........ 700/125 |
| 5,684,344 A | | 11/1997 | Takei |
| 5,693,165 A | * | 12/1997 | Schmitz ...................... 156/164 |
| 5,693,195 A | | 12/1997 | Saito et al. |
| 5,766,406 A | | 6/1998 | Bohn et al. |
| 5,776,289 A | * | 7/1998 | Steidinger ................. 156/273.1 |
| 5,888,343 A | | 3/1999 | Olson |
| 5,895,555 A | | 4/1999 | Van Den Bergh |
| 5,965,963 A | | 10/1999 | Chitayat |
| 5,994,798 A | | 11/1999 | Chitayat |
| 6,022,443 A | | 2/2000 | Rajala et al. |
| 6,086,694 A | * | 7/2000 | Winter et al. ................. 156/64 |
| 6,149,755 A | * | 11/2000 | McNichols et al. ......... 156/264 |
| 6,165,306 A | * | 12/2000 | Rajala ........................ 156/263 |
| 6,450,321 B1 | * | 9/2002 | Blumenthal et al. ..... 198/459.8 |
| 2003/0079330 A1 | | 5/2003 | Stopher et al. |

FOREIGN PATENT DOCUMENTS

| | | |
|---|---|---|
| CH | 678616 A5 | 10/1991 |
| EP | 0 812 789 A3 | 12/1997 |

OTHER PUBLICATIONS

U.S. patent application Ser. No. 09/620,867, Blumenthal.

* cited by examiner

Primary Examiner—Christopher P. Ellis
Assistant Examiner—Mark A. Deuble
(74) Attorney, Agent, or Firm—Jack L. Oney, Jr.; Michael B. Kolodesh; Jay A. Krebs

(57) ABSTRACT

A method and apparatus for receiving parts traveling at a first speed through a receiving zone and applying the parts to a carrier traveling at a second speed through an application zone. The method and apparatus utilizes transferring devices for transporting the parts between the zones. The transferring devices are coupled to programmable servo motors capable of varying the speed of the transferring devices to accommodate the receiving and application processes.

17 Claims, 26 Drawing Sheets

METHOD AND APPARATUS UTILIZING SERVO MOTORS FOR PLACING PARTS ONTO A MOVING WEB

This application is a continuation-in-part of prior application Ser. No. 09/620,867 filed Jul. 21, 2000, now U.S. Pat. No. 6,450,321.

FIELD OF THE INVENTION

The present invention relates to a method and apparatus for receiving discrete parts traveling at a speed and applying the parts to a web or other carrier traveling at a different speed.

BACKGROUND OF THE INVENTION

Disposable absorbent articles, such as disposable diapers, generally have been manufactured by a process where discrete parts or components of different materials, such as leg elastic, waist elastic, tapes and other fasteners have been applied to a continuously moving carrier web. Often, the speed at which the parts are fed from one place in the process onto a carrier web is different from the speed of the carrier web, therefore, the speed of the parts must be changed to match the speed of the carrier web to properly apply the parts without adversely affecting the process or the finished product.

Similarly, labels are typically placed onto articles when the speed at which the labels are fed into the process is not the same as the speed of the article to be labeled. Thus, the speed of the labels must be changed to match the speed of the carrier web to properly apply the parts without adversely affecting the process or the finished product.

Several different conventional methods for changing the speed of a part or component of material such that it can be applied to a continuously moving carrier web have been known to those skilled in the art.

For example, one method has been known as the slip cut or cut & slip method. A web of material, which is traveling at a slower speed than the carrier web, is fed into a knife and anvil roll having a surface speed equal to speed of the carrier web. The material slips against the surface of the anvil roll until the knife cuts it into discrete pieces. The purpose of the slip is to ensure the correct amount of material is metered into the system at the desired tension prior to cutting. As the material is cut into the discrete parts, vacuum in the anvil roll is activated to hold the discrete part on the anvil without slipping, so that the discrete part is accelerated to the speed of the anvil roll. The anvil roll then carries the part to the point where the vacuum is released and the parts are applied to the carrier web while both the parts and the carrier web are traveling at the same speed. The problem with the above method is that the slip process is very sensitive to material properties and process settings. For example, when the coefficient of friction between the material and anvil roll is too high the material will elongate during the slip process. This elongation, if it occurs, can contribute to high variability in the final cut length and placement of the discrete part on the carrier web.

Another method has used festoons to reduce the speed of the carrier web to match the speed of the discrete parts of material to be applied to the web. An example of this method is described in U.S. Pat. No. 5,693,195 issued to Schmitz. The carrier web is temporarily slowed down to the speed of the parts with the excess portion of the carrier web gathering in festoons. The parts of material are then applied to the carrier web while both the parts and the web are traveling at the same speed. The festoons are then released allowing the moving web to return to its original speed. This method has two main drawbacks. First, the carrier web must be festooned and then released; this may damage or otherwise change the properties of the carrier web. Second, the storage system requires a large amount of space in typical disposables production systems because there is a direct relationship between line speed and storage space needed.

Another method has utilized a cam actuated follower arm. The cam actuated follower comprises a cam follower at one end of the arm and a holding plate at the other end of the arm. The cam follower remains in contact with a fixed cam which is mounted concentric with the instantaneous center of rotation of the holding plate. As the holding plate rotates, its radial distance from the center of rotation is increased and decreased to change the surface speed of the holding plate. The discrete parts of material are placed on the holding plate when it is at its smallest radius so that the speeds match. The plate then extends radially enough during the rotation to match the speed of the plate to the speed of the carrier web. At this point the discrete parts are transferred to the carrier web. This method has two main drawbacks. First, the plate is designed to match the curvature of one radius, not both. This means that either the pick-up of the discrete part or the transfer of the discrete part, or both, will occur across a gap for some part of the transfer. This can lead to a loss of control of the discrete part, which impacts handling of parts under tension, such as leg elastics. Second, to achieve the desired change in speed, the mechanical elements typically used, such as cams or linkages, become fairly large to stay within acceptable design limits for accelerations and rise angles. This size leads to increased cost and reduced flexibility, as the unit must be redesigned for each application.

Another method has utilized noncircular gears to change the speed of a transferring device. The means rotates at a constant radius, but the rotational velocity is varied between a minimum and a maximum to pick up the discrete part at its speed and place the part on the carrier web at its speed. This eliminates the size issues and speed or gap mismatch issues, but relies on mechanical means to achieve the change in rotational velocity. The drawback of this is that new transmission parts (gears or other means) are required each time a change in product design occurs that changes placement pitch length, discrete part length, or other key factors. This can be expensive and time-consuming to change. An example of this method is described in U.S. Pat. No. 6,022,443 issued to Rajala and Makovec.

SUMMARY OF THE INVENTION

In response to the discussed difficulties and problems encountered in the prior art a new method and apparatus for receiving discrete parts traveling at a speed, changing the speed of the parts to match the speed of a carrier web or body, and applying the parts to the carrier has been discovered.

In one aspect, the present invention concerns an apparatus for receiving discrete parts traveling at a first speed and applying the parts to a carrier traveling at a second speed. The apparatus comprises at least one rotatable transferring device and one driving mechanism for each transferring device. Each rotatable transferring device comprises at least one shell segment configured to move along an orbital path through a receiving zone where the parts are received and an application zone where the parts are applied to the carrier. The carrier might comprise a continuous moving substrate web, or might be another apparatus such as a drum. The driving mechanism utilizes a programmable motor such as a servo motor to transmit rotational energy to the rotatable transferring device. The driving mechanism may transmit rotational energy to the rotatable transferring device through a direct connection or a transmission interposed therebetween. The transmission may include gear to gear contact or gearboxes.

In another aspect, the present invention concerns an apparatus for receiving discrete parts of an elastic material traveling at a first speed and applying the parts to a carrier traveling at a second speed. The parts of the elastic material might already be at the desired tension and elongation length when the apparatus receives them. On the other hand, the parts of the elastic material might be at a lower tension and elongation length than desired when the leading edge is transferred to the apparatus, but might be stretched during the transfer to the apparatus if the apparatus is traveling at a faster speed than the discrete parts. Alternately, the parts might be at a higher tension and elongation than desired when the leading edge is transferred to the apparatus, but can relax to the desired state if the apparatus is traveling at a slower speed than the discrete parts. The change in tension and elongation can be performed uniformly along the entire length of the discrete material part, or can be intentionally varied during the initial transfer by changing the speed of the rotatable transferring means.

In another aspect, the material fed into the transferring device may comprise a continuous web which might be cut into discrete parts while on the transferring device by a knife, hot wire, laser beam, or other method commonly known. Alternatively, the material fed into the system can be broken into discrete parts by acceleration of the rotatable transferring device. This breaking process can be aided by perforating the material at the desired break point prior to arriving at the receiving zone.

In another aspect, the discrete parts can have adhesive or other bonding material applied to them while traveling on the rotatable transferring device. The rotation speed of the transferring device can be controlled in register with a bonding material applicator such that the bonding material can be applied either intermittently or continuously as the rotatable transferring device rotates.

In another aspect, the discrete parts of material can be modified prior to placement on the carrier to aid in a final bonding process. This modification can come through heat addition, moisture addition, or other known method for altering material properties to aid in the bonding process.

In still another aspect, the programmable motors of the apparatus of the present invention can be arranged in a series wherein each of the motors and the transferring devices(s) actuated by each motor is aligned in relation to a common axis of rotation of all motors and transferring devices.

As compared to conventional methods, such as the cut & slip method described above, for changing the speed of a discrete part so that it can be applied to a carrier, utilizing a programmable motor provides the ability to obtain greater changes in speed, to maintain constant speeds for a fixed duration, and to simplify the set-up process when changing from one product to another. Thus, the use of programmable motors can provide a more precise control of the length and placement of the part onto the carrier while offering great flexibility in the type of parts that are to be made.

BRIEF DESCRIPTION OF THE DRAWINGS

The present invention will be more fully understood and further advantages will become apparent when reference is made to the following detailed description of the invention and the accompanying figures. The figures are merely representative and are not intended to limit the scope of the appended claims.

FIG. 9b is a side view of the apparatus shown in FIG. 9a.

DETAILED DESCRIPTION OF THE INVENTION

The present invention provides a method and apparatus for receiving discrete parts traveling at a first speed and applying the parts to a carrier traveling at a second speed. The apparatus and method are particularly useful for applying any part to a carrier useful in the making of disposable absorbent articles or for placing labels onto articles. It is readily apparent, however, that the method and apparatus would be suitable for applying any part to a substrate web or carrier of parts.

Figure 1:
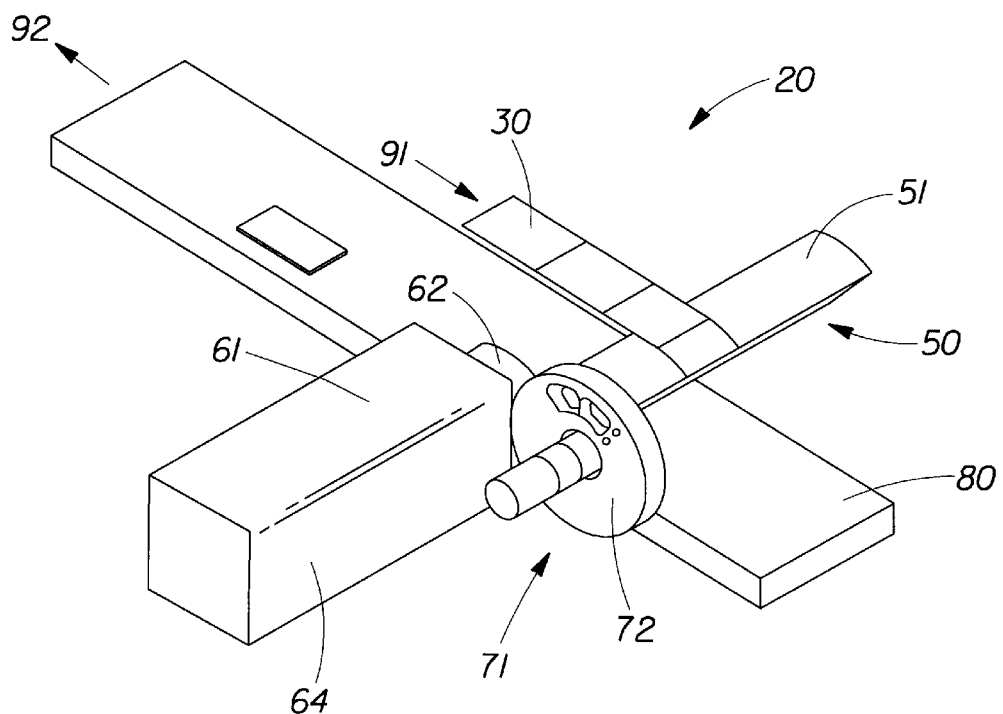
FIG. 1 representatively shows an isometric view of one example of an apparatus of the present invention.
Figure 2:
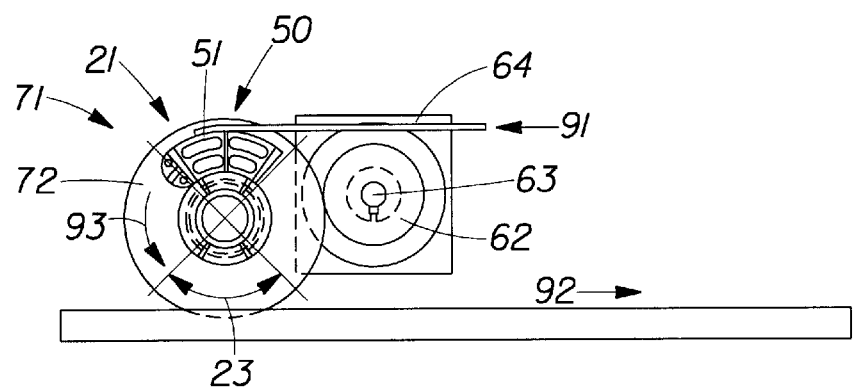
FIG. 2 representatively shows a schematic side view of the apparatus in FIG. 1.

Referring now to FIGS. 1 and 2, there is representatively shown an aspect of the invention wherein an apparatus generally indicated at 20 receives discrete parts 30 traveling at a first speed in the direction indicated by the arrow 91 associated therewith and applies the parts 30 to a carrier 80 traveling at a second speed in the direction indicated by the arrow 92 associated therewith. The illustrated example of the apparatus 20, as representatively shown in FIGS. 1 and 2, further comprises a driving mechanism 61 for transmitting rotational energy to a driven mechanism 71. The driving mechanism 61 includes a connection to the driven mechanism using any technique known to those skilled in the art such as, for example, gear to gear connection, transmission belting and pulleys, gearboxes, direct couplings, and the like or any combinations thereof. For example, in FIG. 1 the driving mechanism is connected to a driving gear 62 which transmits rotational energy to a driven gear 72 connected to the driven mechanism 71. In use, the driving gear 62 engages and rotates the driven gear 72 which, in turn, rotates the transferring device 50.

The illustrated example of the transferring device 50 comprises at least one shell segment 51 connected to the driven mechanism 71. The shell segment 51 of the transferring device 50 can be connected to the driven mechanism 71 by any technique known to those skilled in the art such as, for example, bolts, screws, pins, keys and matching keyways, connector parts such as shafting or brackets, welding and the like or combinations thereof. For instance, the shell segment 51 shown in FIG. 1 is connected directly to the driven gear 72 by fitting the end of the shell segment 51 into a mating hole in the driven gear 72 and locking it into position with a pin. Similarly, other components of the apparatus 20 can be connected together employing the above described assembly techniques.

The dimensions of the shell segment 51 may vary depending upon the desired output of the apparatus 20 and the size and shape of the discrete articles 30 being transferred. The shell segment 51 may comprise a crescent-shaped member having an outer, peripheral arc length spanning from about 5 degrees to about 340 degrees, an outer radius ranging from about 25 mm to about 500 mm, and a width ranging from about 50 mm to about 750 mm. As the driven mechanism 71 rotates, the transferring device 50 travels in the direction indicated by the arrow 93 as shown in FIG. 2. The circumferential, outer peripheral surface of the shell segment 51 defined by an outer radius, travels along and defines an orbital path that passes through a receiving zone 21 and an application zone 23. The receiving zone 21 and the application zone 23 are defined by the respective regions of the orbital path traveled by the shell segment 51.

The illustrated example of the driving mechanism 61 includes a rotatable circular driving gear 62 connected to an input shaft 63. In this example, the input shaft 63 is the output shaft of the motor 64. The driven mechanism 71 is placed parallel to the driving mechanism 61 such that the driving gear 62 meshes with the driven gear 72 using gear set-ups known to those skilled in the art. In use, the motor 64 rotates the input shaft 63 which rotates the driving gear 62 which, in turn, rotates the driven gear 72 and transferring device 50.

Alternatively, the driven mechanism 71 may include any mechanism known to those skilled in the art by which rotational energy can be conducted from one shaft to another such as, for example, v-belts, timing belts, continuous chains and the like or combinations thereof. Further, the driven mechanism 71 may include any mechanism known to those skilled in the art by which input velocity can be variably modified to an output source such as, for example, cams, linkages, and the like or combinations thereof as long as the changes in rotational speed are substantially created by the motor 64.

It will be further appreciated that the method and apparatus 20 of the invention can utilize one or, in the alternative, two, three or more combinations of transferring devices 50, driven mechanism 71, driving mechanism 61 and motor 64 in series to achieve the desired application of the discrete parts to the carrier. The different combinations may allow the use of a continuously moving web to supply the discrete parts. In addition, greater speed ratio differentials may be achieved by using combinations of transferring devices, driven mechanisms, driving mechanisms and motors in series.

Figure 3:
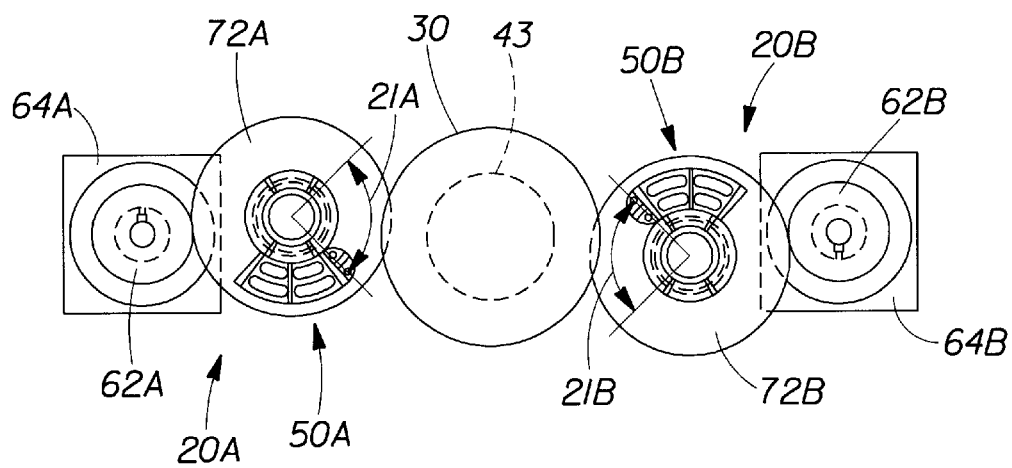
FIG. 3 representatively shows a schematic side view of the apparatus used in the present invention arranged in series.

It will be further appreciated that the method and apparatus 20 of the invention, when used in series, do not need to operate at the same receiving zone 21 and application zone 23. For example, referring to FIG. 3, there is representatively shown one apparatus 20A comprising one transferring device 50A connected to a motor 64A by a driving gear 62A and driven gear 72A and a second apparatus 20B comprising one transferring device 50B connected to a motor 64B by a driving gear 62B and a driven gear 72B. Apparatus 20A uses receiving zone 21A to accept parts 30 from a drum 43 while apparatus 20B uses receiving zone 21B to accept parts 30 from the same drum 43 at a different rotational position on said drum.

Figure 4:
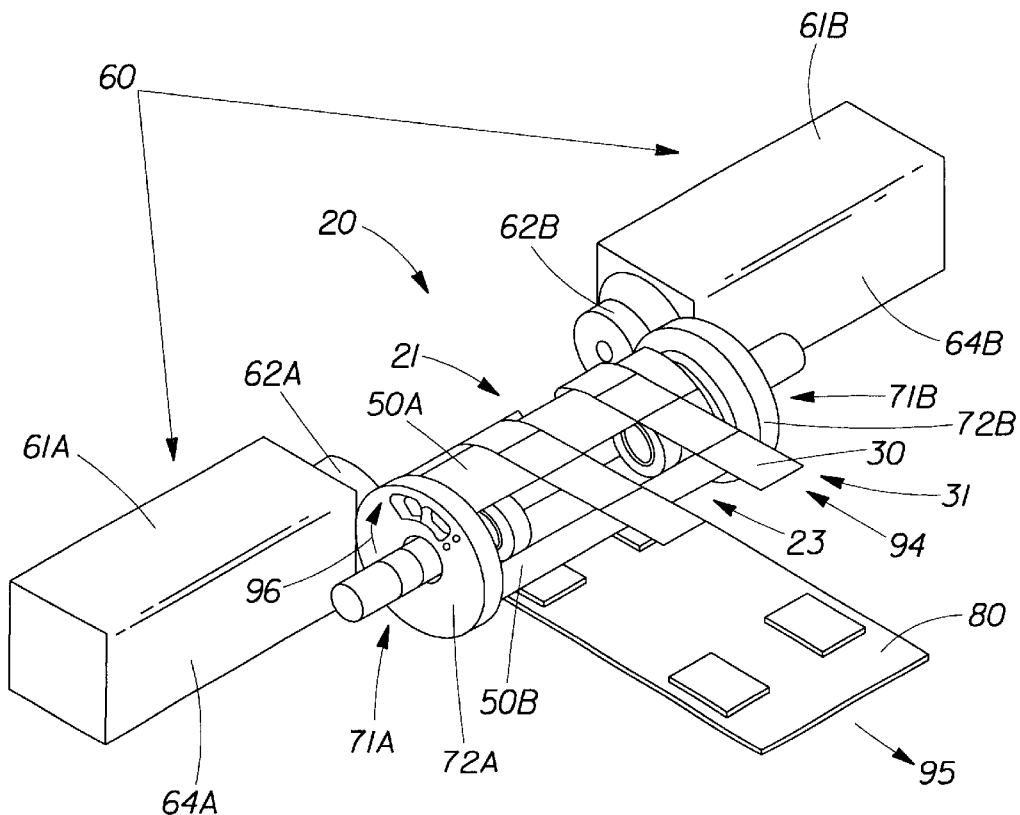
FIG. 4 representatively shows a perspective view of an apparatus according to the present invention comprising two transferring devices.

Another aspect of the invention shown in FIG. 4 comprises an apparatus 20 receiving discrete parts 30 of a web of an material 31 traveling at a first speed in the direction indicated by the arrow 94 associated therewith and applies the parts 30 to a carrier 80 traveling at a second speed in the direction indicated by the arrow 95 associated therewith. The illustrated example of the apparatus 20 comprises two rotatable transferring devices, represented by 50A and 50B, for receiving and applying the parts 30. The apparatus 20 further comprises a driving system 60 having two driving mechanisms 61A and 61B, each of which includes a motor 64A, 64B and a driving gear 62A, 62B for transmitting rotational energy to the driven mechanism 71A, 71B represented by the driven gear 72A, 72B.

As illustrated in FIG. 4, each transferring device 50A and 50B comprises a shell segment 51A, 51B connected to a driven gear 72A, 72B. As each gear rotates, the transferring devices 50A, 50B travel in the direction indicated by the arrow 96 associated therewith. In use, the circumferential, outer peripheral surface of the shell segments 51A, 51B travels along and defines an orbital path that passes through a receiving zone 21 and an application zone 23 defined by the respective regions of the orbital path traveled by the shell segments 51A, 51B of transferring devices 50A and 50B.

The size and shape of the shell segments 51A and 51B may vary as the number of shell segments per transferring device changes. For example, if the apparatus includes two transferring devices as representatively illustrated in FIG. 4, each shell segment 51A and 51B may have an outer peripheral arc length which spans from about 5 to about 175 degrees of the orbital path of the transferring devices 50A and 50B.

Each driven mechanism 71A, 71B may include any mechanism known to those skilled in the art by which rotational energy can be conducted from one shaft to another such as, for example, v-belts, timing belts, continuous chains and the like or combinations thereof. Further, the driven mechanisms 71A, 71B may include any mechanism known to those skilled in the art by which input velocity can be variably modified to an output source such as, for example, cams, linkages, and the like or combinations thereof as long as the changes in rotational speed are substantially created by the motor 64. Alternatively, a first driven mechanism may connect to a first transferring device using a first shaft from a driven gear, and a second driven mechanism may be connected to a second transferring device using concentric shafting around the first shaft.

Figure 5:
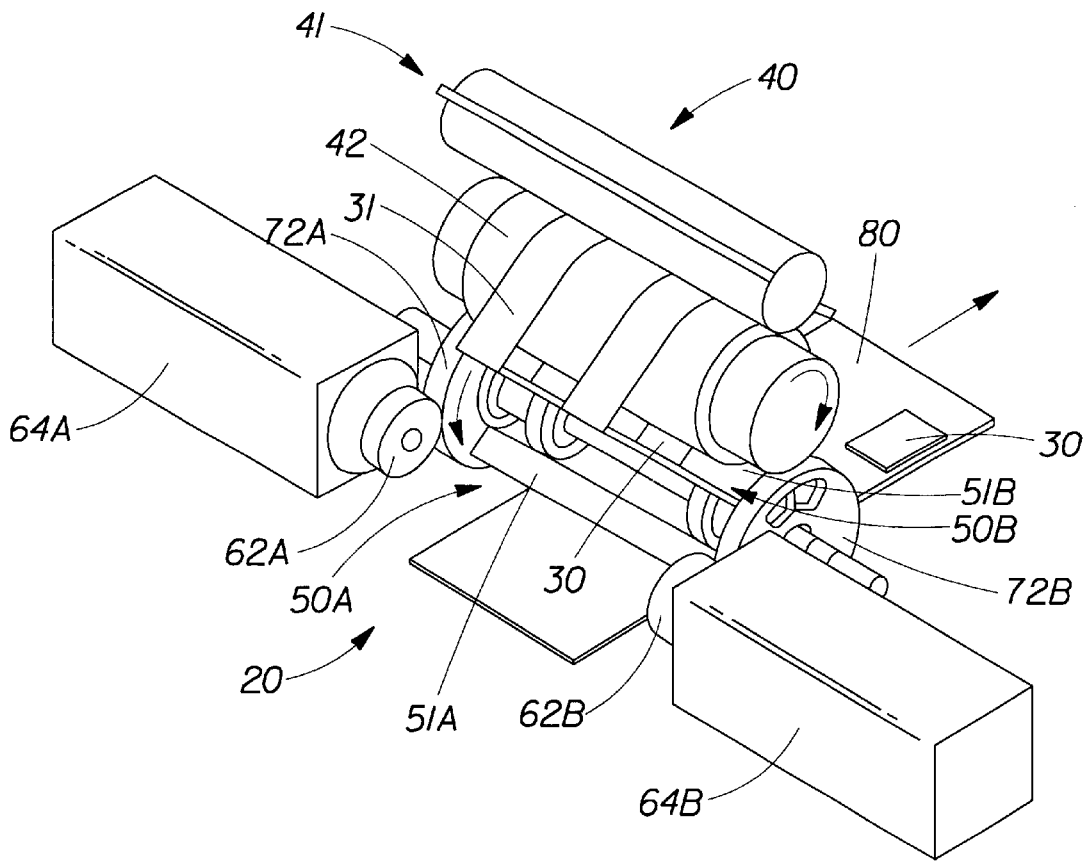
FIG. 5 representatively shows a perspective view of the apparatus shown in FIG. 4 including a cutting device.

The apparatus 20, as representatively illustrated in FIG. 5, may further comprise a cutting device 40 comprising a pinch knife cutter 41 and a knife anvil 42 to sever the continuously moving web of material 31 into discrete parts 30 prior to or concurrent with the transfer of the discrete parts to the shell segments 51A, 51B of the transferring devices 50A, 50B. The pinch knife cutter 41 may comprise a rotary cutter as shown or any other mechanism known to those skilled in the art capable of severing a web of material into discrete parts. In certain aspects of the invention, the knife anvil 42 may be omitted and the pinch knife cutter 41 can be made to sever the web as it is held on the shell segment of the transferring device. Alternately, the continuously moving web of material may be placed directly on the shell segments of multiple transferring devices so that the web lies on multiple segments at once allowing for the planned acceleration of one device to generate a force necessary to sever a single part from the web. Such severing may be facilitated by perforating the web upstream of the receiving zone so that the parts break at a desired perforation during acceleration.

For receiving the parts in the receiving zone, the transferring device, as representatively illustrated in the various configurations of the invention, may further include a gripping mechanism so that the outer concave surface of the shell segment can capture a part in the receiving zone and transport the part to the application zone. For this embodiment, the gripping mechanism may include a vacuum that can be selectively imposed through ports in the shell segment leading to the outer concave surface. For instance, the vacuum may be activated in the receiving zone to seize the parts and deactivated in the application zone to release the parts to the carrier. In this manner, positive control is maintained over the parts at all times during the transfer process. Alternatively, the gripping mechanism may include any technique known to those skilled in the art for gripping and releasing parts such as, mechanical clamps, electrical clamps, magnetic clamps and the like or combinations thereof.

For transferring the parts to the carrier in the application zone, the apparatus may comprise any of a variety of options known to those skilled in the art such as, adhesive applied on the part, adhesive applied on the carrier, electrostatic charge between the part and carrier, vacuum on the carrier and the like or combinations thereof. Alternately, the transfer can include the generation of a weld between the part and the carrier by any of a variety of means known to those skilled in the art such as, pressure generation at a nip formed between the shell segment and the carrier at transfer, interaction between a pattern on the shell segment and an ultrasonic horn behind the carrier at transfer, and the like, or combinations thereof. In addition, in order to aid the welding process, the part may be modified on the shell segment by energy addition using any mechanism known to those skilled in the art such as, for example, hot air currents, ultraviolet lighting, laser bombardment and the like or combinations thereof The use of a programmable motor in the apparatus, as representatively illustrated in the various aspects of the invention described above, provides an inexpensive and adaptable method for receiving parts 30 traveling at a speed and applying the parts to a carrier 80 traveling at a different speed. The variable angular velocity is produced by varying the current supplied to the motor. Since the driven mechanism is coupled to the output of the motor, changes in the angular velocity and position of the motor directly correlate to changes in the angular velocity and position of the transferring device. The current supplied to the motor can be controlled using any of a variety of a methods for programming motors known to those skilled in the art such as, standard cam curve functions, a reference data table containing reference points, desired motor encoder points, and the like or combinations thereof.

The means of supplying the rotational movement required can be achieved in a plurality of methods to those skilled in the art. The programmable electric motors can be driven from any known power source that is capable of delivering a modulated signal such that the motor torque can be varied proportionally. The number of motors included per a transferring device can be any suitable number. Each motor attached to a single transferring device can be supplied by one or more power sources capable of delivering a modulated torque signal. The torque signal is typically an electrical current which may be fed to the individual motors by separate power supplies or by a single power supply and controlled by a plurality of methods to those skilled in the art.

The actual position of the transferring device can be controlled in a plurality of methods to those skilled in the art The control system demonstrated utilizes a programmable system that incorporates a position feedback from the transferring device and motor. The position feedback device on the transferring device, or motor, may or may not be required if the position of the transferring device can be inferred by other means known to those skilled in the art. The typical position transducer is an encoder, or resolver based system, but any system that can be constructed to provide the actual position, or the inferred position of the transferring device can be used.

The demonstrated control system is one of many kinds, models, and technologies that can be used to supply the proportional signal to the motor power supplies that will generate the modulated torque signal.

The control system may or may not be integrated into the motor power supply. The control system, along with the motor power supply, may or may not be integrated into the motor itself. The control system may or may not be digitally controlled, and may be constructed in various methods, and configurations known to those skilled in the art. The control system, power supplies, feedback devices, and motor devices, and any other components required for the purpose of providing rotational movement are hereafter referred to as the "drive system" for the transferring device.

The drive system will be capable of continuously controlling the position of the transferring device, and allowing the transferring device to stay in phase to a given position on the recipient product, web, or host machine. The drive system will be capable of following speed transitions or position variations on the recipient product or web, by phasing itself, when necessary, to the recipient product, web, or host machine, with or without operator intervention. The drive system will allow for the registration of the patch on the transferring device in relation to the recipient product or web, either upstream or downstream of the transferring device.

The drive system may be capable of providing for a plurality of control methods and algorithms known to those skilled in the art for the purpose of providing motion and position control that will allow the transfer of a patch to a recipient product or web. The drive system may be capable of changing the patch length with or without operator intervention, for the purpose of varying product sizes or continuous patch length, or position variation control. The position reference for the drive system maybe a pre-calculated cam profile, continuously calculated profile, or any positional trajectory generation algorithm known to those skilled in the art and may be either digital or analog based. The motion trajectory for the transferring device may be based on a pre-calculated profile or a profile that is modified by the speed of the recipient product or web.

Figure 6:
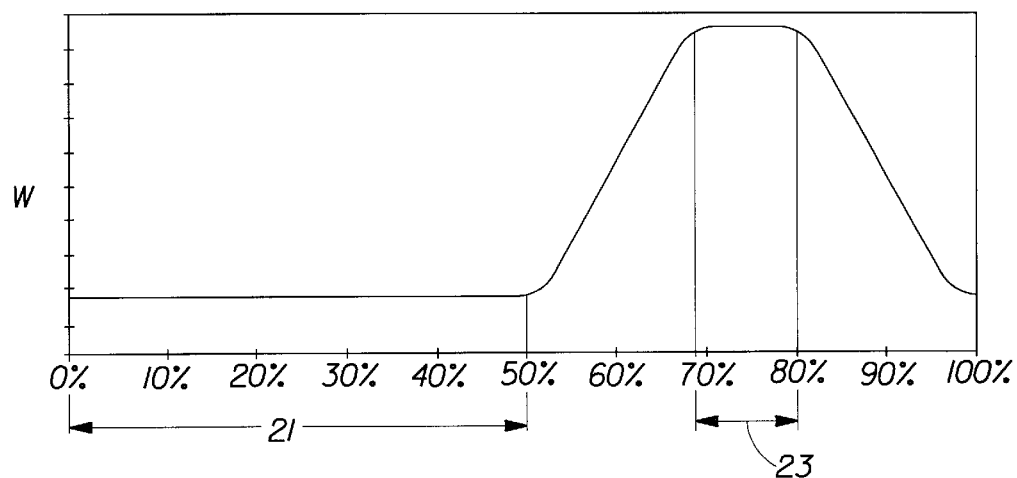
FIG. 6 representatively shows a speed profile for a typical motor output.
Figure 7:
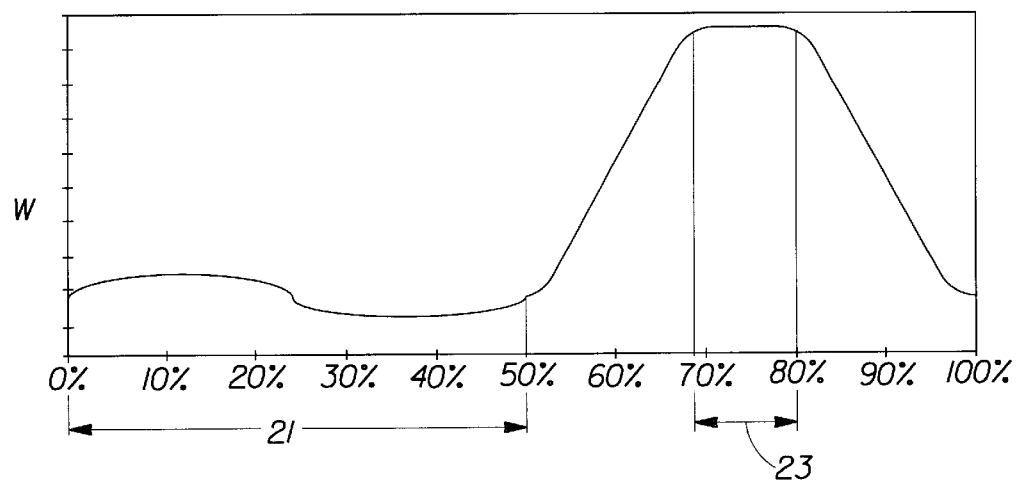
FIG. 7 representatively shows an alternate speed profile for a motor output wherein one of the fixed speed regions has been changed to variable speed.

The speed profile of a typical motor setting is representatively illustrated in FIG. 6. As shown, the programmable motor 64 used to drive the transferring device 50 of the present invention can provide variable angular velocities including periods where the velocity remains constant for a fixed duration. These constant velocity dwell times can be advantageous in the receiving zone 21 and the application zone 23 particularly when the pick up and transfer occurs over substantial arc lengths of contact. Alternatively, one or more of the constant speed regions can be changed to a controlled variable speed region as representatively illustrated in FIG. 7. This would enable the part 30 to be picked up in the receiving zone 21 at a variable speed, which, when the part 30 is elastic, would allow tensions to be varied incrementally therein which may be desirous in certain product features. In another example, the constant speed of the motor 64 in the application zone 23 can be such that the corresponding speed of the transferring device is different from speed of the carrier at transfer. Such speed variations generate tension in the part 30 by incrementally transferring the part 30 in a controlled manner from one means traveling at one surface speed to a second means traveling at a second surface speed.

It will be further appreciated that the velocity of the transferring device 50 outside of the application zone or the receiving zone can be tailored to aid the performance of secondary processes including adhesive application, printing of identification or registration marks, application of bonding aids, moisture addition and the like and combinations thereof Such changes in velocity may be beneficial by presenting specific velocity profiles or even additional periods of constant velocity, which would allow for more precise interaction with the secondary processes being performed.

Programmable motors, such as those used in the present invention, can be purchased from any number of suppliers of programmable motors such as Rockwell Automation, located in Milwaukee, Wis. Further, the program inputs to the motors can be generated by one of ordinary skill in the art if provided with the analytical representation of the desired output function as representatively illustrated in FIG. 6. For instance, the creation of the electronic cam profile for the motor can be developed by first determining the key input variables. The key input variables are based on desired product features, the base design of the apparatus 20 and the desired cycle speed of the apparatus 20. Secondly, the radius of the outer surface of the transferring device 50 is determined. Once the radius is determined, the required cam inputs of rotational velocities, distances traveled and time available for acceleration can be calculated, which serve as the input to the cam profile generator. For example, in a system with the following inputs:

N=the number of transferring devices 71 used in the apparatus 20

H=the number of shell segments 51 per transferring device 71

$L_{s,parts}$=distance from lead edge of first part 30 received in a given transfer to transferring device 50 to lead edge of part 30 received in the next cycle of transfer to a transferring device 50 in the apparatus 20

$L_{s,product}$=distance from lead edge of first product zone on carrier 80 to which parts 30 are applied in a given transfer from transferring device 50 to lead edge of product zone on carrier 80 to which parts 30 are applied in the next cycle of transfer from a transferring device 50 in the apparatus 20

$V_{min}$=average surface speed of the shell 51 on the transferring device 50 in receiving zone 21

$V_{max}$=average surface speed of the shell 51 on the transferring device 50 in application zone 23

$\tau$=cycle time of a given lane of product making $\tau_R$=time in receiving zone 21, typically of value $\tau$ when $V_{min}$=incoming speed of parts 30

$\tau_A$=time in application zone 23, typically of value Ratio * $\tau$ when $V_{max}$=speed of carrier 80 The following dependent variables can be computed:

Ratio=$L_{s,parts}/L_{s,product}$

Radius=distance from effective center of rotation of transferring device 50 to outer surface of shell 51 on transferring device 50

$\tau_{TRANS}$=time in transition from $V_{min}$ to $V_{max}$=N*$\tau$-$\tau_R$-$\tau_A$=(N-1-Ratio) *$\tau$ $\omega_{min}$=average angular velocity of transferring device 50 in receiving zone 21=$V_{min}$/Radius $\omega_{max}$=average angular velocity of transferring device 50 in application zone 23=$V_{max}$/Radius $\theta_{min}=\omega_{mm}*\tau_R=\omega_{min}*\tau$ $\theta_{max}=\omega_{max}*\tau_A=\omega_{max}*$ Ratio *$\tau$ $\theta_{transition}=2*\pi/H-\theta_{min}-\theta_{max}=2*\pi/H-\omega_{min}*\tau-\omega_{max}*$ Ratio *$\tau$ The Radius may be determined by assuming that the average angular velocity, $\omega_{ave}$, of the transferring device 50 during the transition from the receiving zone 21 to the application zone 23 is equal to $(\omega_{min}+\omega_{max})/2$. This means that the distance traveled during the transition $\theta_{transition}=\omega_{ave}*\tau_{TRANS}$. However, $\theta_{transition}$ must also be equal to $2*\pi/H-\theta_{min}-\theta_{max}$. Consequently, by setting the two equations for $\theta_{transition}$ equal to one another the following expression for Radius is defined.

Radius=$(L_{s,part}*(N+1-Ratio)+L_{s,product}*(N-1+Ratio))*H/(4*\pi)$

It is important to note that $L_{s,part}$ as defined can be different from the overall length of the par, for example, when the edges of the part are cut at some angle which is not perpendicular to the direction of flow of the part. The above equations and parameters must be solved slightly differently to account for this.

Now, given the inputs, one of ordinary skill can determine $\tau_{TRANS}$, $\omega_{min}$, $\omega_{max}$, $\theta_{min}$, $\theta_{max}$, and $\theta_{transition}$ which are typical inputs needed for electric cam software programs. The generic cam programs would then create the input table for the motor 64. Note that the Radius is an optimal radius, and not the only possible radius for the set of inputs. The Radius is optimal because it uses the entire transition time for changing the angular velocity of the transferring device 50. By changing the Radius, the actual amount of time required to change speed must change or else the combined conditions of change in angular velocity and change in angular acceleration will not be met. The amount by which the Radius can deviate from the optimum can be changed from optimal depends upon the torque requirements of the system under the new accelerations at the given speed and the capability of the selected motor 64.

Alternately, one of ordinary skill could generate the input table for the motor without the aid of software programs. For example, the cam profile for cycloidal motion having dwells of constant velocity comprises a minimum velocity equal to $\omega_{min}$, a change in velocity, $\Delta\omega$, equal to $\omega_{max} - \omega_{min}$, and a rise time $\beta$ of the motion equal to $\tau_{TRANS}/2$. The resulting function of angular position is as follows:

$\theta_{act} = \omega_{min} * T$ when $0 \le$ time in cycle, $T \le \tau_R$ $\theta_{act} = \omega_{min} * T + \frac{1}{2} * \Delta\omega * \beta * ((T-\tau_R)/\beta - \sin((T-\tau_R)*\pi/\beta)/\pi)$ when $\tau_R < T < \tau_R + \beta$ $\theta_{act} = \omega_{min} * T + \frac{1}{2} * \Delta\omega * \beta + \omega_{max} * (T - \tau_R - \beta)$ when $\tau_R + \beta \le T \le \tau_R + \beta + \tau_A$ $\theta_{act} = \omega_{min} * T + \frac{1}{2} * \Delta\omega * \beta + \omega_{max} * \tau_A + \frac{1}{2} * \Delta\omega * \beta * ((T - \tau_R - \beta - \tau_A)/\beta - \sin((T - \tau_R - \beta - \tau_A)*\pi/\beta)/\pi)$ when $\tau_R + \beta + \tau_A < T \le \tau$ Profiles other than the cycloidal profile can be found in Machinery's Handbook, the 25th Edition.

If a radius is chosen for the transferring device that is not optimum, the transferring device will accomplish the desired changes in velocities, however, the timing for such changes will not correspond to that which is desired. For instance, if the Radius is slightly greater than optimal, using the equations above, the actual distance traveled during the transition is less than needed to position the transferring device 50 at the start of the application zone 23 even though the transferring device 50 achieves the desired angular velocity.

Figure 8A:
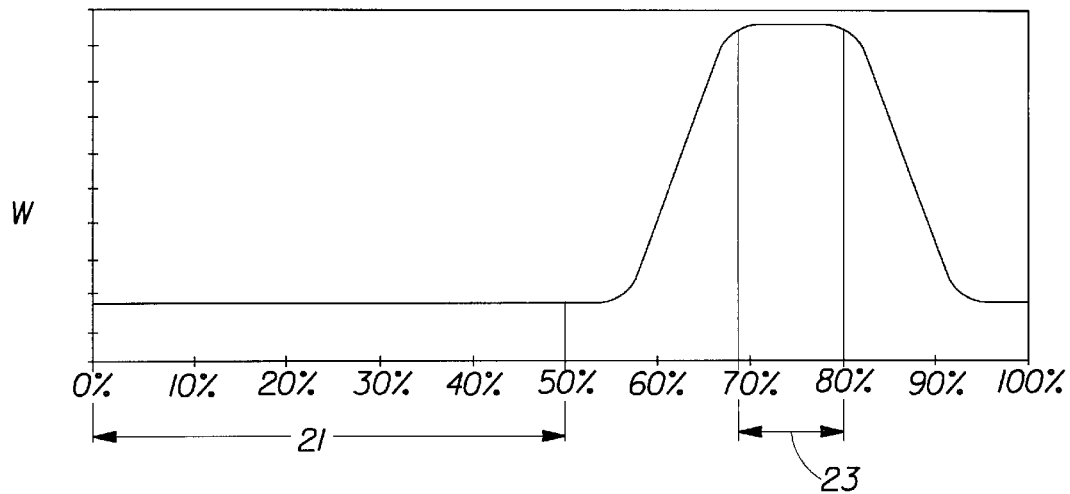
FIG. 8A representatively shows an alternate speed profile for a motor output wherein the rise time $\beta$ has been decreased to allow for a non-optimal radius without changing the maximum or minimum rotational velocity in the system.
Figure 8B:
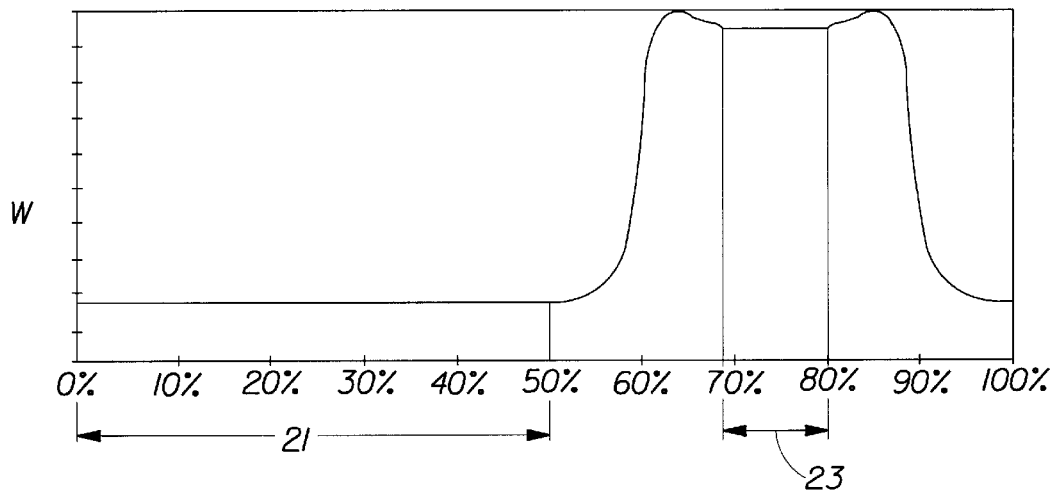
FIG. 8B representatively shows an alternate speed profile for a motor output wherein the maximum rotational velocity during the period of transition from receiving to application zone exceeds the average rotational velocity in the application zone to allow for a non-optimal radius.
Figure 8C:
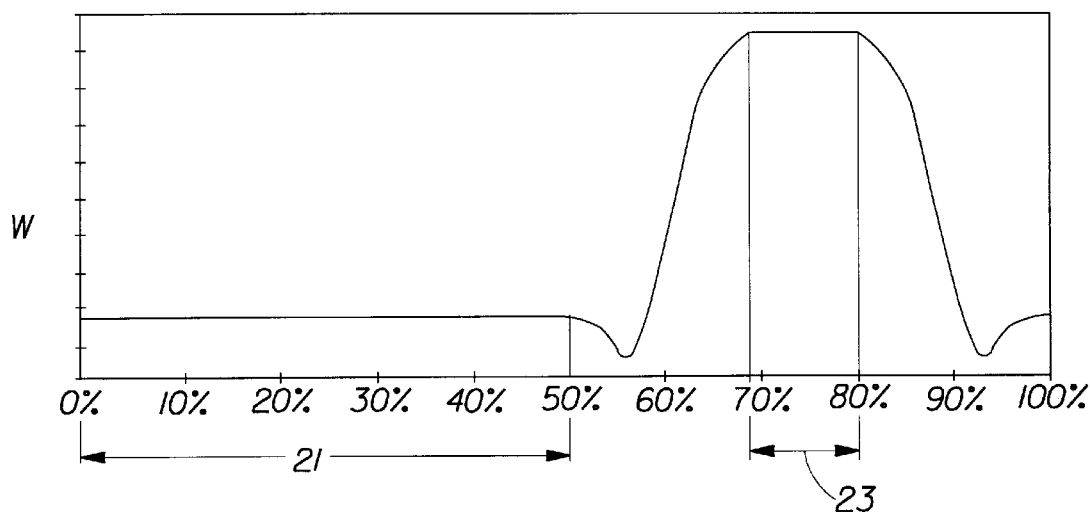
FIG. 8C representatively shows an alternate speed profile for a motor output wherein the minimum rotational velocity during the period of transition from receiving to application zone is less than the average rotational velocity in the receiving zone to allow for a non-optimal radius.

There are at least three possible ways to achieve speed profiles accommodating pick up and transfer using a non-optimal Radius. First, the rise time $\beta$ can be decreased by spending more time at $\omega_{min}$ as shown in FIG. 8A. Secondly, as shown in FIG. 8B, the maximum angular velocity in the transition zone can be greater than the $\omega_{max}$ in the application zone 23. Thirdly, the minimum angular velocity in the transition zone can be less than the $\omega_{min}$ in the receiving zone 21 as shown in FIG. 8C.

Using the same cam formulas, one can determine the maximum accelerations generated during the motion using the same family of cam profiles. For example, for the cycloidal profile used above, the peak acceleration is $(\Delta\omega * \pi)/(2 * \beta)$. This is important because, for high speed applications, the limiting design factor in the apparatus 20 is motor 64 torque capability at the desired angular velocities. One of ordinary skill in the art can determine total torque requirements for the apparatus 20 for a given application based on the masses and radii of gyration for the different components of the apparatus 20 and the expected accelerations.

As compared to conventional methods for changing the speed of a discrete part so that it can be applied to a continuously moving carrier (such as the slip cut method described above), the use of programmable motors provides the ability to obtain greater changes in speed and to maintain constant speeds for a fixed duration. The fixed speed dwell achieved by programmable motors can be accurately and quickly generated to control the length and placement of the parts. In comparison to the noncircular gear method described above, the use of programmable motors provides the ability to change the profile at will without requiring the fabrication of new parts.

For example, in the various aspects of the invention, the profile generated by the programmable motor 64 is analytically designed such that the rotatable transferring device 50 receives the parts 30 in the receiving zone 21 while maintaining a constant surface speed substantially equal to the speed of the parts 30. Moreover, the output profile of the motor 64 is designed such that the surface speed of the rotatable transferring device 50 changes to a second constant surface speed as the rotatable transferring device 50 moves from the receiving zone 21 to the application zone 23. The term "surface speed," as used herein, refers to the speed of the circumferential, outer peripheral surface of the shell segment 51. The output profile of the motor 64 can be designed such that the speed of the parts 30 being transferred is substantially equal to the speed of the carrier 80 as the parts are applied to the carrier in the application zone 23. The surface speed of the shell segment 50 is maintained substantially constant in the receiving zone 21 and in the application zone 23 from at least about 0 to about 300 degrees of rotation, desirably from about 5 to about 300 degrees of rotation, and more desirably from about 5 to about 240 degrees of rotation of the transferring device 50. In addition, the surface speed increase or decrease of the shell segment 51 as it moves from the receiving zone 21 to the application zone 23 defines a speed ratio of from at least about 100:99 to about 50:1, desirably from about 20:19 to about 25:1, and more desirably from about 10:9 to about 20:1. The term "speed ratio", as used herein, defines the ratio of the surface speed of the shell segment 51 as the parts 30 are applied to the carrier 80 in the application zone 23 to the surface speed of the shell segment 51 as the parts 30 are received in the receiving zone 21.

It has been described above how the required torque and angular speed of the apparatus determine the needed motor capability. For high speed applications common in the manufacture of articles such as diapers, training pants, among other uses, the peak torque requirements of the apparatus 20 combined with the resulting acceleration at the motor 64 will require very high torque to inertia properties in the motor 64. Motors capable of such flux densities are typically of rare earth permanent magnet design or more powerful, and can be purchased from manufacturers of motors such as Rockwell Automation located in Milwaukee, Wis.

In some embodiments it may be necessary to have more than one shell segment per transferring device driven by a single motor, particularly where the process includes secondary operations that are preferably performed at constant speed (see below). It may also be necessary to have multiple shell segments per transferring device in order to increase the radius from the center of rotation to the arcuate outer surface of the shell segments. The radius of a transferring device having a single shell segment may be so small that secondary parts of the design (such as porting airflow for vacuum across the shell segment) may be impractical. Based on the equation above for determining Radius, adding shell segments per transferring device results in an increase in Radius. For example, increasing the number of shell segments per transferring device from one to three triples the Radius.

Additional shell segments also result in an increase in motor torque which is determined from the following expression.

$$T = I_{motor} * \alpha_{motor} + I_{load} * \alpha_{motor} * (N_{driving}/N_{driven})^2$$

where $I_{motor}$—is the moment of inertia of the motor including anything connected directly to the motor shaft.

$\alpha_{motor}$—is the angular acceleration of the motor $N_{driving}/N_{driven}$—the ratio of the number of teeth on the driving gear to the number of teeth on the driven gear.

$I_{load}$—is the moment of inertia of the load (including the transferring device).

The additional shell segments result in an increase in mass moment of inertia of the transferring device, $I_{load}$. Inertia is a direct function of mass and radius of gyration squared. For a transferring device having three shell segments, the mass can be expected to approximately triple and the radius of gyration can be expected to nearly double. Consequently, the moment of inertia of the transferring device can be expected to be at least ten to twelve times the inertia of an equivalent system having a single shell segment. The increase in inertia results in a decrease in the rotational velocity by a factor of three in a system having three shell segments per transferring device, consequently, the gear ratio, $N_{driving}/N_{driven}$ is increased by a factor of three in order to maintain the required motor acceleration. Overall, the resultant torque requirement for the system having three shell segments per transferring device is 11% greater relative to a transferring device having one shell segment per transferring device. Given that motor capability is the key limiting design factor, an increase of 11% in required torque can be significant and can potentially limit the capacity and application of the apparatus.

Figure 9A:
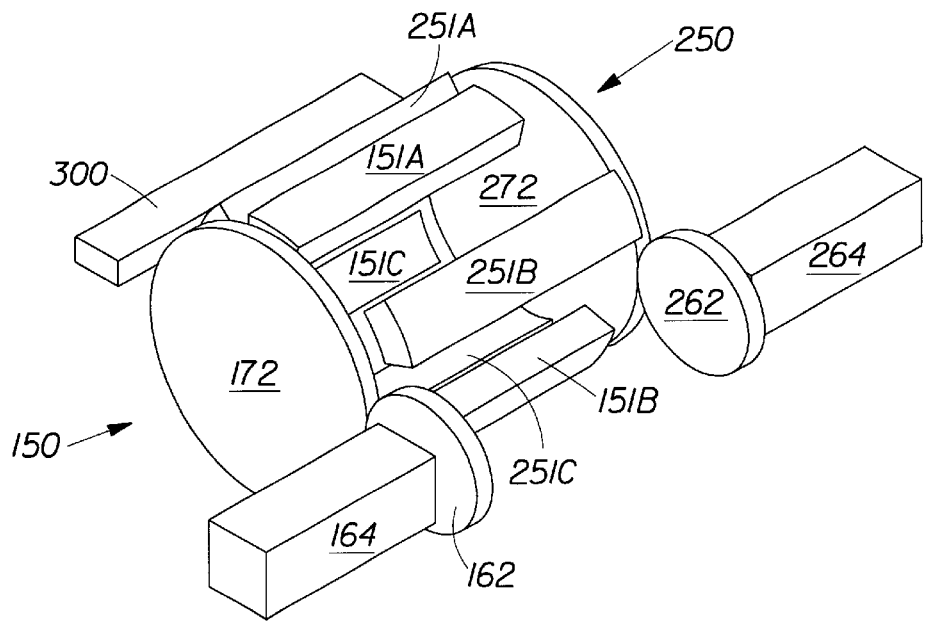
FIG. 9a representatively shows a perspective view of an apparatus according to the present invention including an applicator for accomplishing a secondary process on the parts, and two transferring devices comprising multiple shell segments.
Figure 9B:
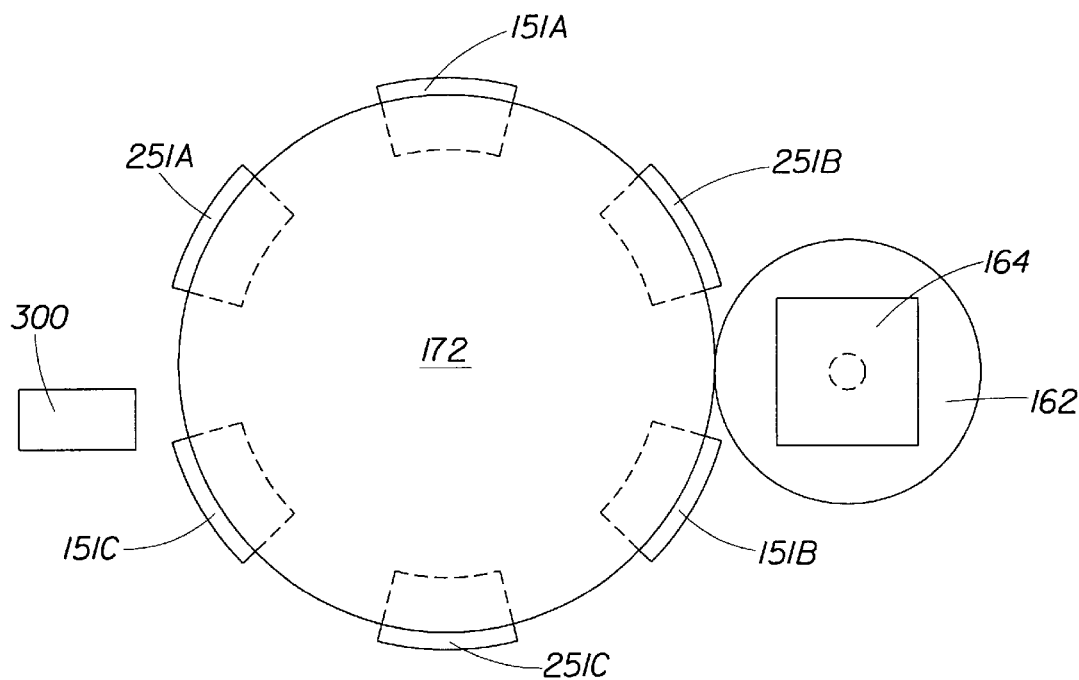

There is no restriction on the number of shell segments per motor besides space and inertial concerns, however, the arrangement pattern of multiple devices is limited. For instance, a transferring device having two shell segments per motor cannot be arranged such that any two shell segments on one transferring device are adjacent to one another in sequence without at least one shell segment from a separate transferring device driven by a separate motor interposed between them. FIGS. 9a and 9b portray an apparatus according to the present invention including an applicator for performing a secondary process on the parts and two transferring devise 150 and 250, each having multiple shell segments. Transferring device 150 comprises three shells 151A, 151B, and 151C and transferring device 250 comprises three shells 251A, 251B, and 251C. Each transferring device is driven by a separate motor 164, 264. As shell segment 151A of transferring device 150 collects a part in the receiving zone 21, the surface speed of shell segments 151A, 151B and 151C are each equal to the receiving speed while the surface speeds of shell segments 251A, 251B, and 251C of transferring device 250 are each equal to either the application speed or some other transitional speed.

Transferring devices comprising two or more shell segments are particularly beneficial where the process includes secondary processes where it is necessary for the part to be moving at a constant speed. As previously described, a secondary process step can be performed on the part such as adhesive application, printing, heating, or moisture application at any point between the receiving zone and the application zone. However, it is preferred to perform the secondary process while the part is moving at constant speed. In applications where the parts are received as a continuous web with no scrap separating the parts during separation, it is preferred that no gaps occur between adjacent shell segments during the transfer in the receiving zone. For instance, where the secondary process involves the application of an adhesive, it is preferred that the parts move at a constant speed during the application with no gaps in between parts so that the metering rate of the adhesive can be constant and not intermittent.

In order to perform a secondary process on the part at a constant speed with no gaps, the secondary process can be performed on the part before the transferring device starts to accelerate. In other words, the time at the receiving speed is lengthened so that the full arc length of the shell segment of the transferring device (assuming that the entire length of the part is required) passes through the process. For example, if the process involves application of an adhesive, then the entire arc length passes underneath the nozzle of the adhesive applicator. This presents a challenge for a transferring device comprising a single shell segment driven by a single motor since the sum of the receiving time, the application time, and the time for the secondary process might exceed the total cycle time. This problem may be resolved by adding a second transferring device having a single shell segment driven by a separate motor or by using a transferring device having more than one shell segment per transferring device.

In the process, generally, as one shell segment finishes receiving a part, the next shell segment in sequence starts receiving a part Generally, the parts entering the transferring device are part of a continuous web having no spacing in-between at the receiving zone. Consequently, in order to have a no gap situation, shell segments in the receiving zone should have no gap between them. However, in reality, variability in motor positioning, head dimensions, gear backlash, etc. can cause the position of the transfer device to have some variability in rotational position resulting in gaps or even forcible contact therebetween. The above problem can be resolved by the embodiments of the present invention described hereinbelow.

Figure 10:
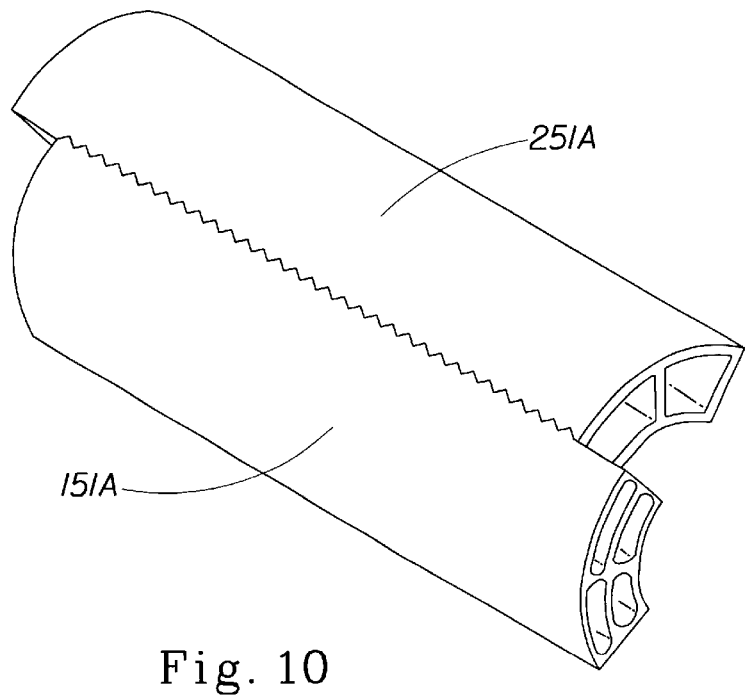
FIG. 10 representatively shows an isometric view of adjacent shell segments according to the present invention having grooved leading and trailing edges that mesh.

First, the shell segments can be fabricated to be a little shorter in arc length than the part to be received, and then the devices can be brought close but not contacting each other. This avoids contact, but does not allow for complete control of the lead and trail edges of the part. This may or may not impact product quality, depending on the part properties. Second, the shell segments can have a shock-absorbing structure on the lead and/or trail edges, so that contact does not generate damage. Depending on the desired cycle life of the transfer device, this might be as simple as placing a compressible foam or as complex as a spring-loaded wall. Third, the shell segments can have mating surfaces which allow the devices to coexist radially and tangentially but not axially. As shown in FIG. 10, shell segments 151A and 215A can have grooved or otherwise modified leading and trailing edges that mesh with similarly modified edges on adjacent shell segments.

It should be understood by one skilled in the art that the embodiments of the present invention having a driven mechanism placed parallel to a driving mechanism described hereinabove are limited to a number of transferring devices and/or a number of heads per a transferring device and/or a number of independent motors per a transferring apparatus. First, this is due to the increasing mechanical complexity associated with providing sufficient stiffness for the shafts rotating the transferring devices because in order to provide more than two rotating transferring devices sharing the same axis of rotation per an apparatus there will be more than one rotating transferring device per a side of the carrier web and the shafts driving the transferring devices located on the one side of the carrier web will be arranged concentrically to each other and thus, the diameters and/or wall thicknesses of the concentric shafts will diminish as the number of transferring devices on the one side of the carrier web increases. Second, as described therein above, as the number of shell segments per a transferring device increases, the torque requirements for the system increases. Third, the number of independent motors driving a transferring device is limited by the physical space available around the transferring device.

Figure 11:
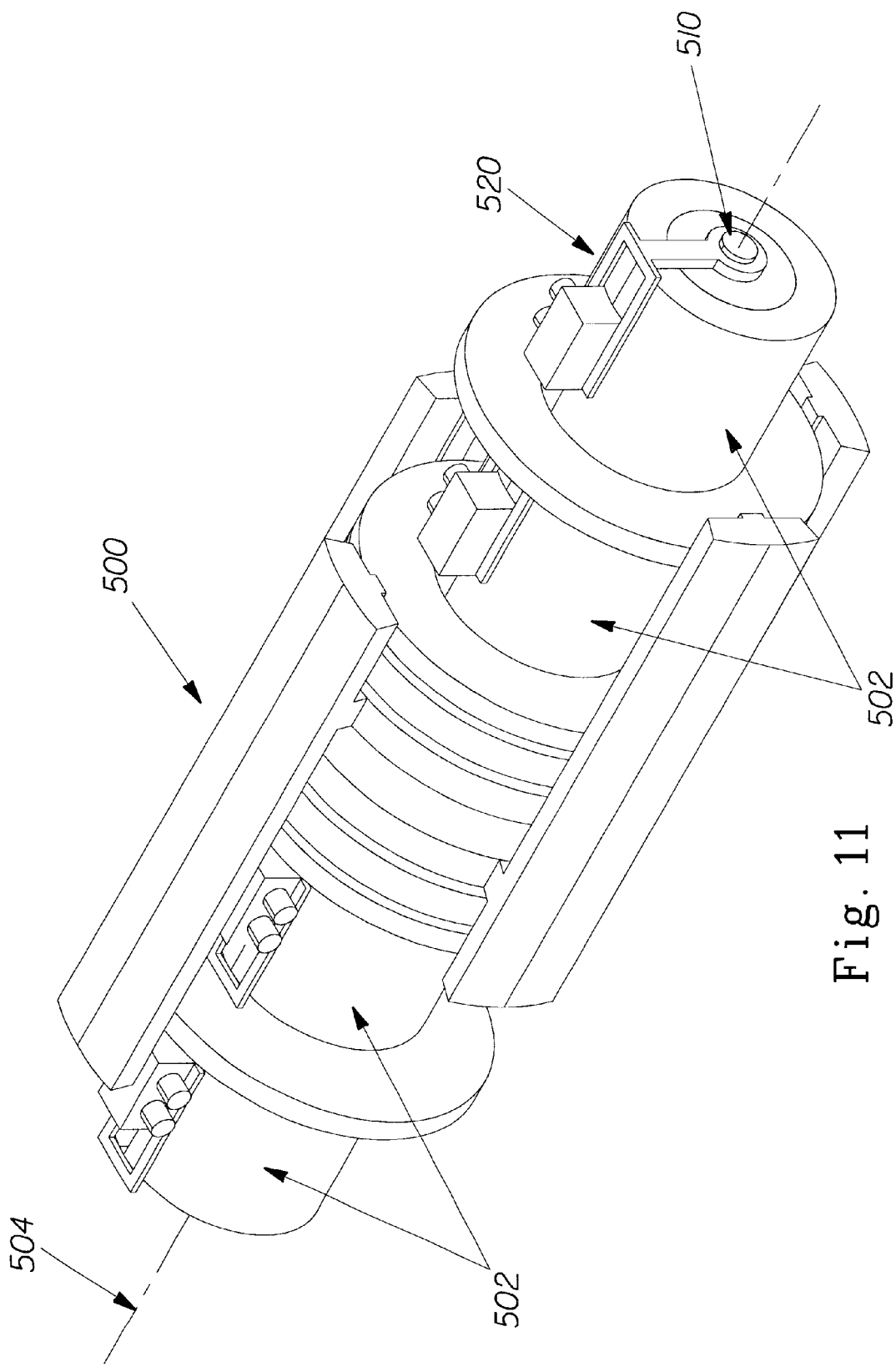
FIG. 11 representatively shows an isometric view of another embodiment of the present invention including a series of motors aligned with a common central axis and wherein each of the motors has a hollow rotatable shaft.
Figure 12:
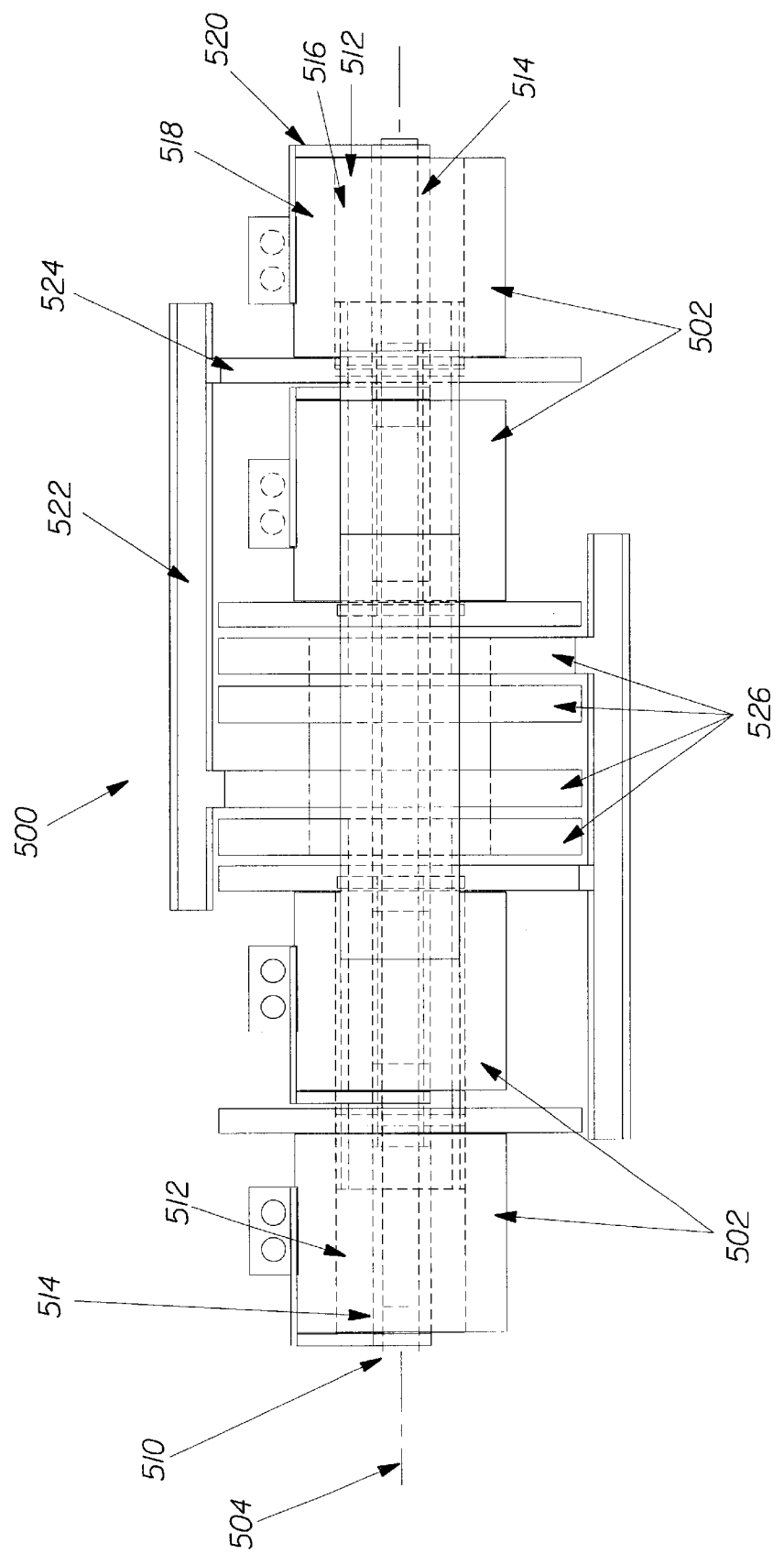
FIG. 12 representatively shows a plan view of the embodiment shown in FIG. 11.

Referring now to FIGS. 11–12 showing an apparatus 500 of the present invention having a series of four motors 502 aligned with a common axis 504. The number of motors can be any suitable number. Each of the motors 502 has an outer stationary stator 518, an inner rotatable rotor 516, and a hollow shaft 512 rotatable with the inner rotor 516. The hollow shaft 512 can be positioned on bearings 514 to enable the hollow shaft 512 to rotate in relation to the stationary central shaft 510. The bearings 514 can be any suitable bearing. In order to maintain the stator 518 stationary, the stator 518 can be connected to the stationary central shaft 512 via a bracket 520. The motors 502 can be purchased from Kolhmorgen Inland Motor of Radford, Va.

Each of the hollow rotatable shafts 512 is linked to a transferring device 522 via a rigid transmitting mechanism 524 to enable the transferring device 522 to rotate together with the hollow rotatable shaft 512 around the common axis 504. The rigid transmitting mechanism 524 can be attached to the hollow rotatable shaft 512 and the transferring device 522 by any suitable means. The transferring device 522 can be supported by a bearing 526 which can be supported by the stationary central shaft 510. The bearing 526 can be any suitable bearing. Alternatively, if desired, the transferring device 522 can be attached to a second motor 502 to provide increased driving capability and/or structural support for the transferring device. Further, alternatively, the transferring device 522 can be driven by any desirable number of motors.

Figure 13:
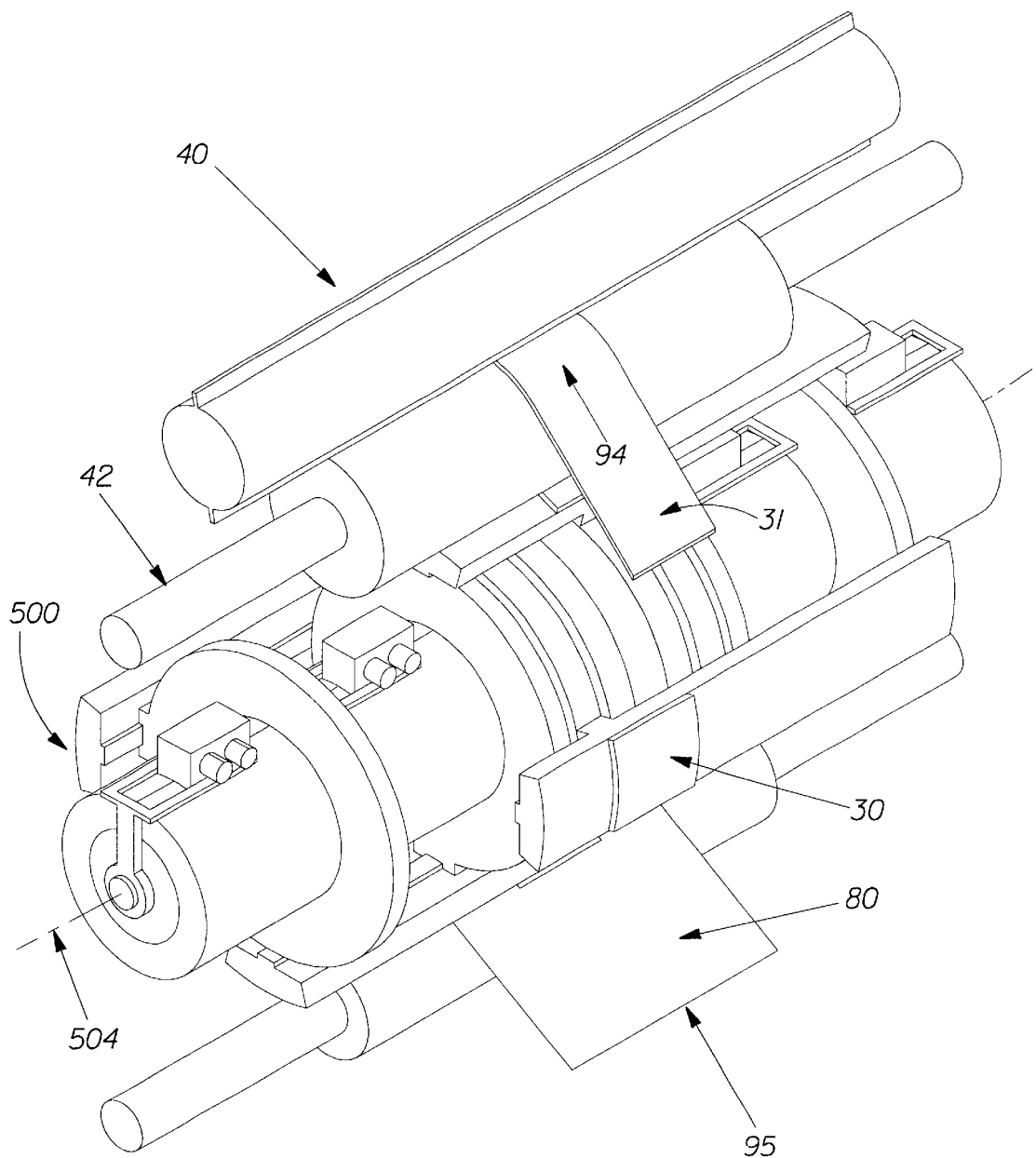
FIG. 13 representatively shows an isometric view of the embodiment shown in FIGS. 11–12 in combination with a cutting device as viewed from upstream.
Figure 14:
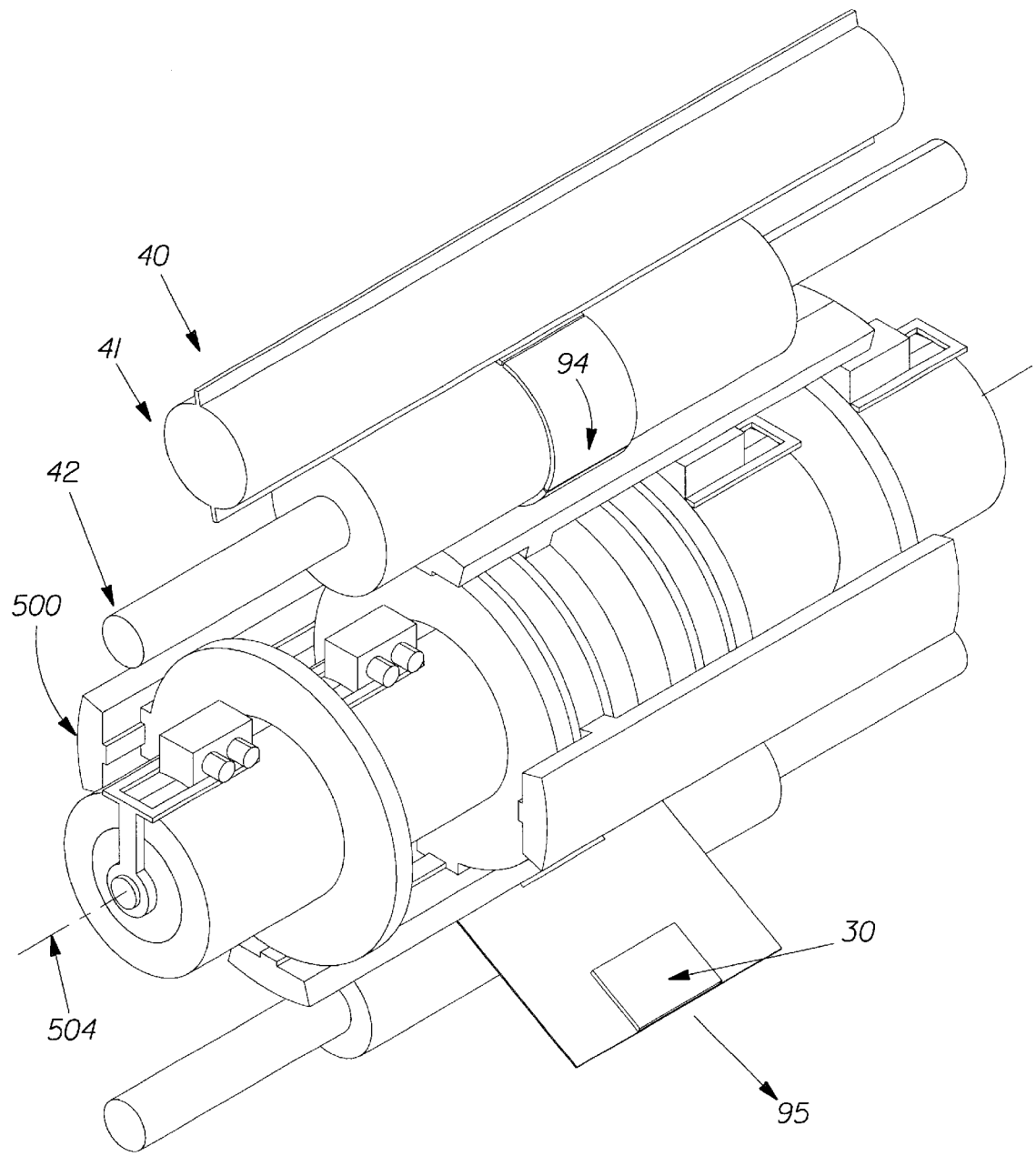
FIG. 14 representatively shows an isometric view of the embodiment shown in FIGS. 11–12 in combination with a cutting device as viewed from downstream.
Figure 15:
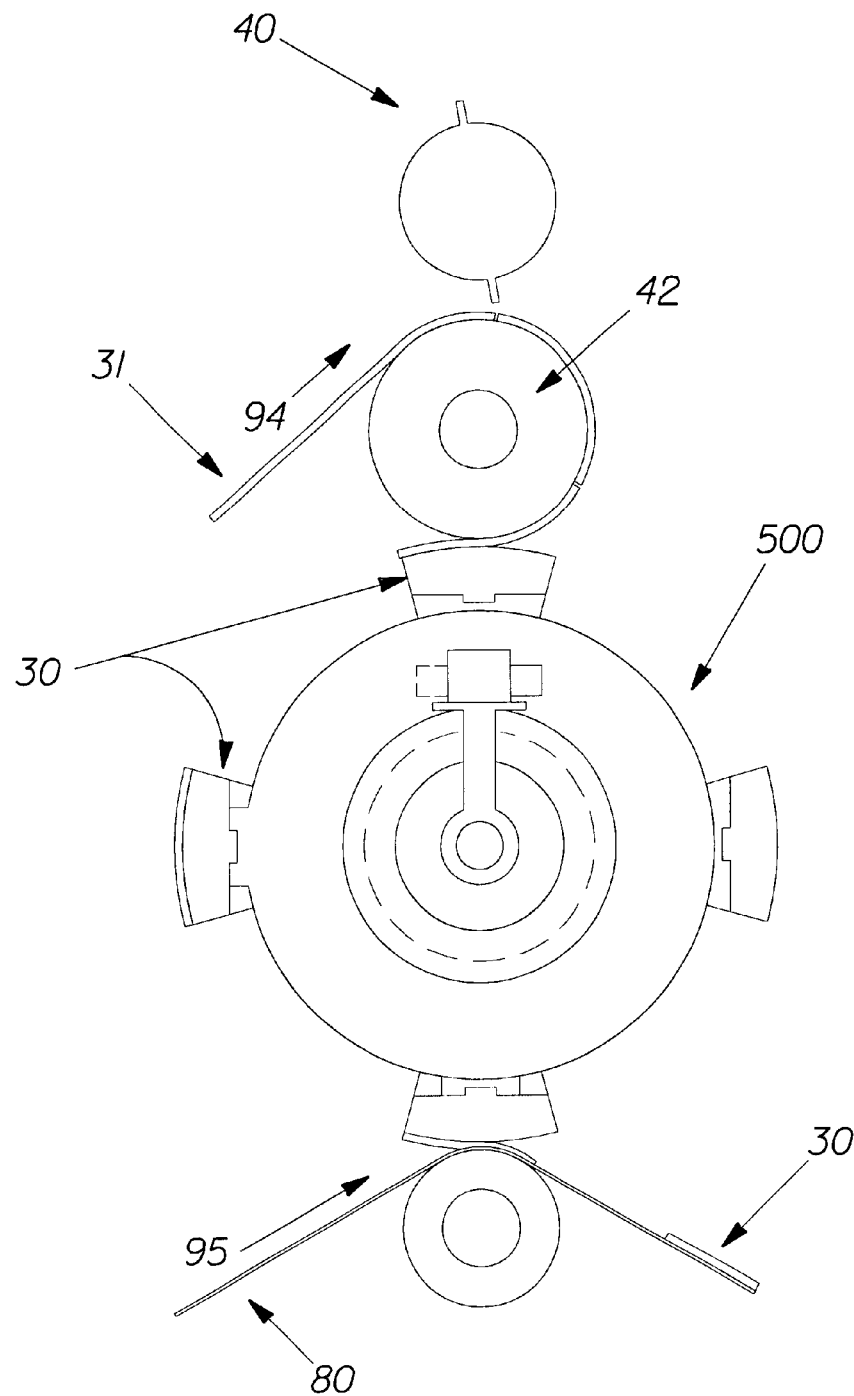
FIG. 15 representatively shows a side view of the embodiment shown in FIGS. 13 and 14.

FIGS. 13–15 illustrate an example of how the apparatus 500 can be used in combination with the cutting device 40 (previously shown in FIG. 4), similarly in all or any aspects to the cutting application described in detail hereinabove, including the alternative omission of the anvil roll 42 and the alternative severing of the material web 31 by a speed differential between adjacent transferring devices.

Figure 16:
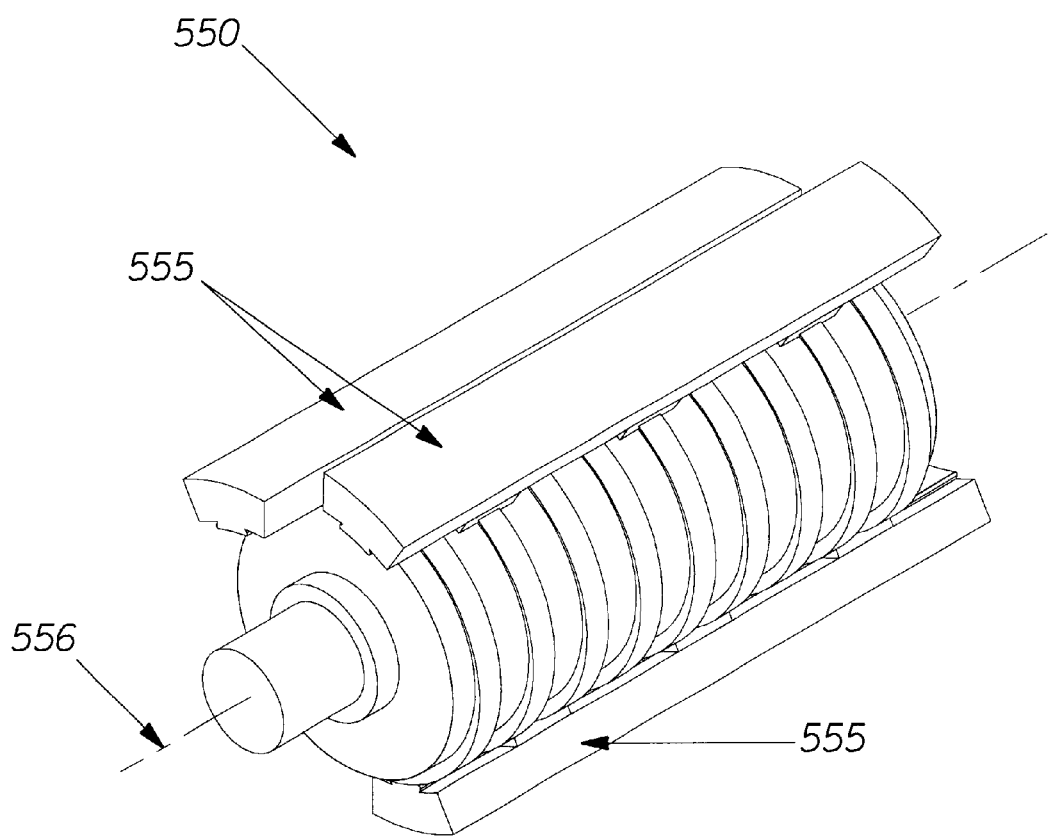
FIG. 16 representatively shows an isometric view of another embodiment of the present invention including a series of motors aligned with a common central axis and wherein each of the motors has at least one stationary track rail and a movable rider.
Figure 17:
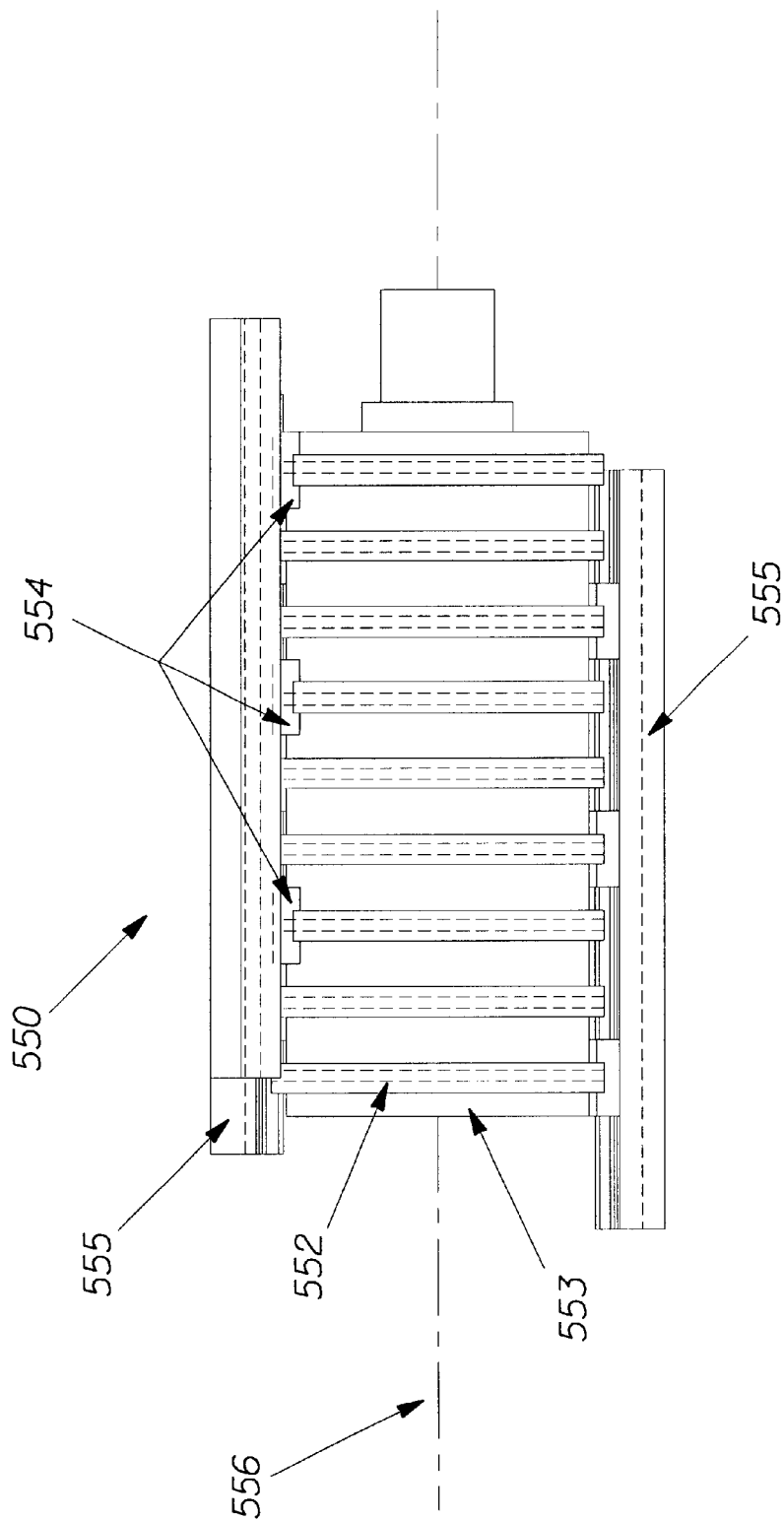
FIG. 17 representatively shows a plan view of the embodiment shown in FIG. 11.
Figure 18:
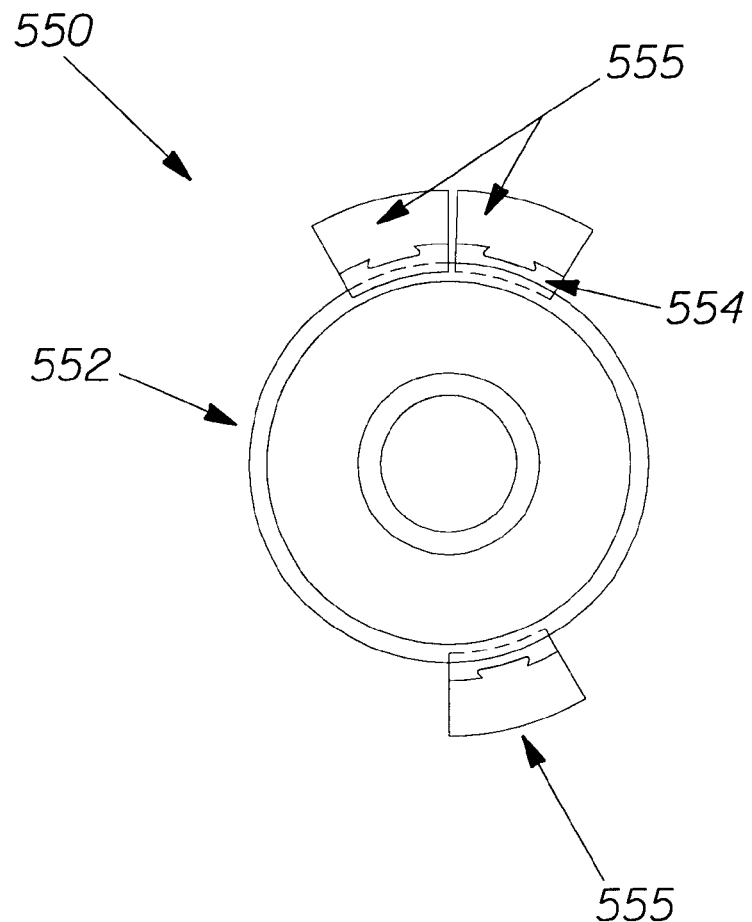
FIG. 18 representatively shows a side view of the embodiment shown in FIGS. 16 and 17.

FIGS. 16–18 illustrate another embodiment of an apparatus 550 of the present invention forming a series of nine motors 551 aligned in relation to the central common axis 556. The motor 551 is generally known as a linear motor having a stationary track 552 forming a path 553 and at least one rider 554 movable on the stationary track 552 on the path 553. The motor 551 can be any suitable linear motor, including linear motors available from Anorad Corporation of New York. For example, the stationary track 552 can include armature windings and/or magnetic materials. The rider 554 can be a permanent magnet, coils, or combinations thereof. The rider is attached to the transferring device 555 for moving the transferring device 555 around the central common axis 556. The number of riders attached to the transferring device can vary from a single rider 554 to a multiplicity of riders 554, either controlled independently or jointly. As shown in FIGS. 16–18, each transferring device 555 is moved by three riders 554.

Figure 19:
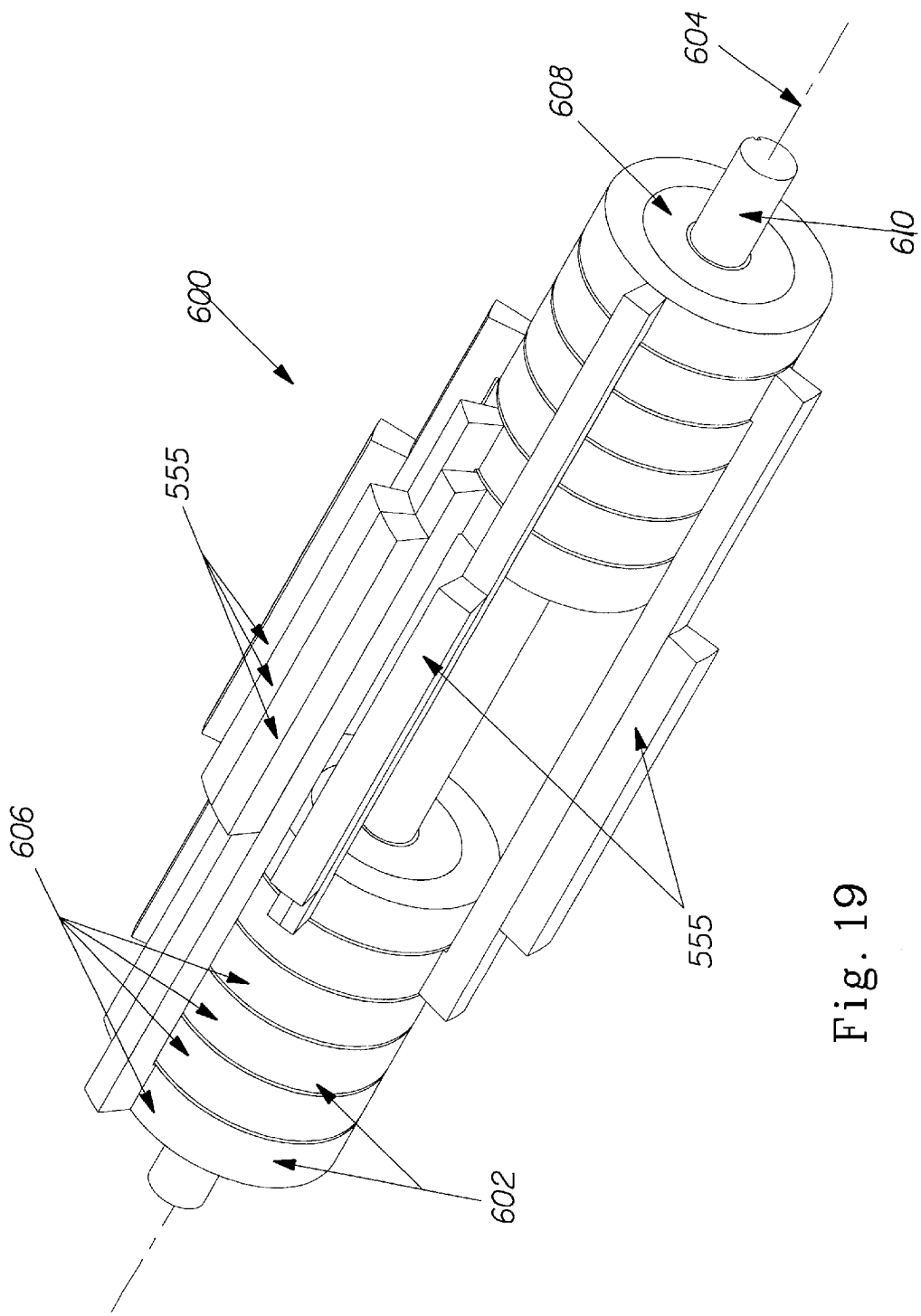
FIG. 19 representatively shows an isometric view of another embodiment of the present invention including a series of motors aligned with a common central axis and wherein each of the motors has a stationary inner stator and a rotatable outer rotor.

FIG. 19 illustrates another embodiment of an apparatus 600 of the present invention forming a series of twelve motors 602 aligned in relation to a central common axis 604. The motor 602 can be any conventional motor having a rotatable outer rotor 606 and a stationary inner stator 608. As shown, each stator 608 is attached to a stationary central shaft 610, however, the motors 602 can be aligned without the use of the central shaft 610, for example, by connecting the motors 602 sideways to each other, directly or indirectly, via inner stationary stators 608. Each of the outer rotors 606 can be directly or indirectly attached to one or more of the transferring devices 550 for moving the transferring device in a programmed motion.

Alternatively, the apparatus of the present invention can include other types of programmable electrical motors suitable to provide a rotational motion of the outer component of the motor. For example, the motors wherein the stator and rotor are disposed parallel to each other as opposed to the concentric arrangements of the motors described therein above.

Figure 20:
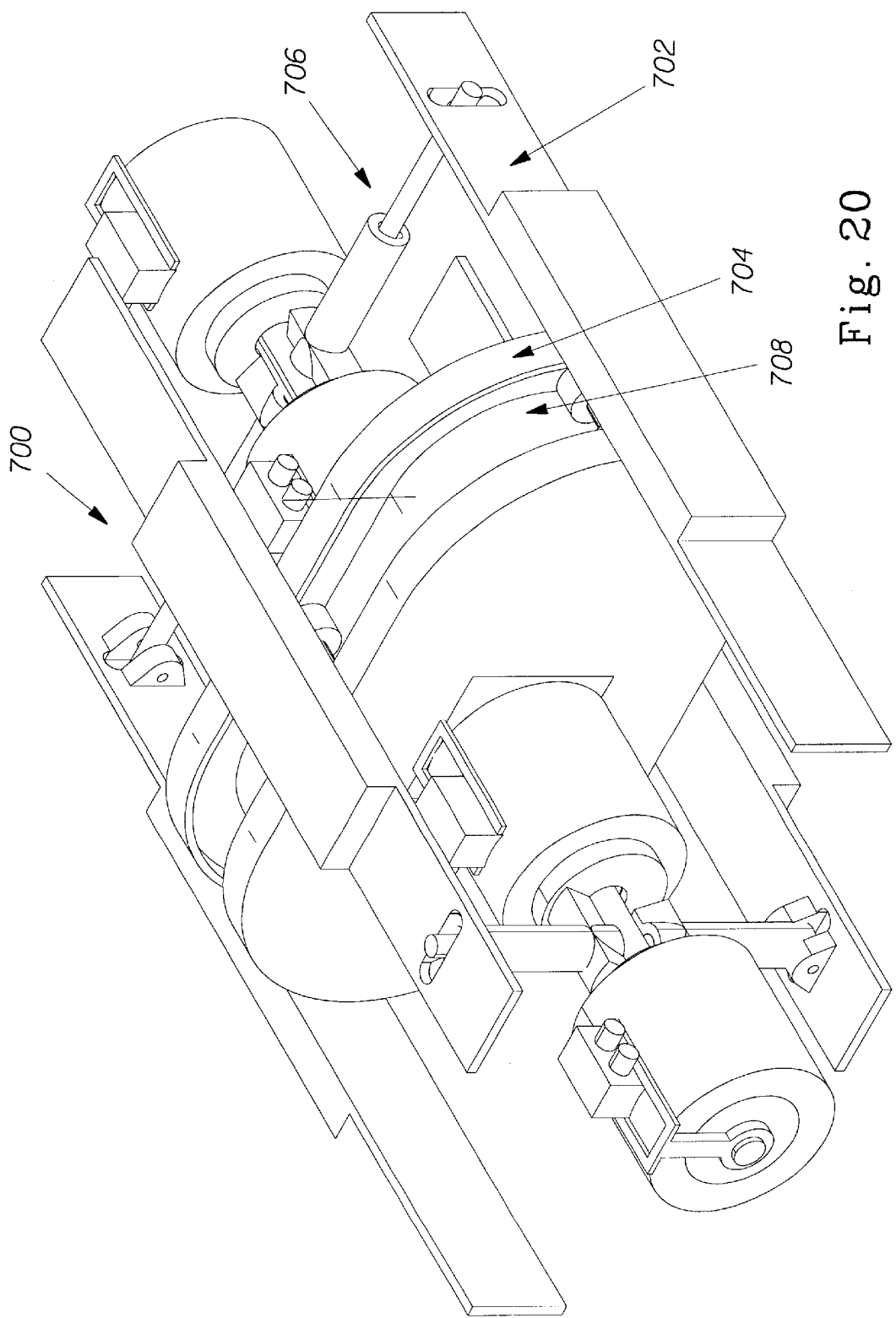
FIG. 20 representatively shows an isometric view of another embodiment of the present invention including a series of motors aligned with a common central axis and wherein each of the transferring devices follows an orbital path.
Figure 21:
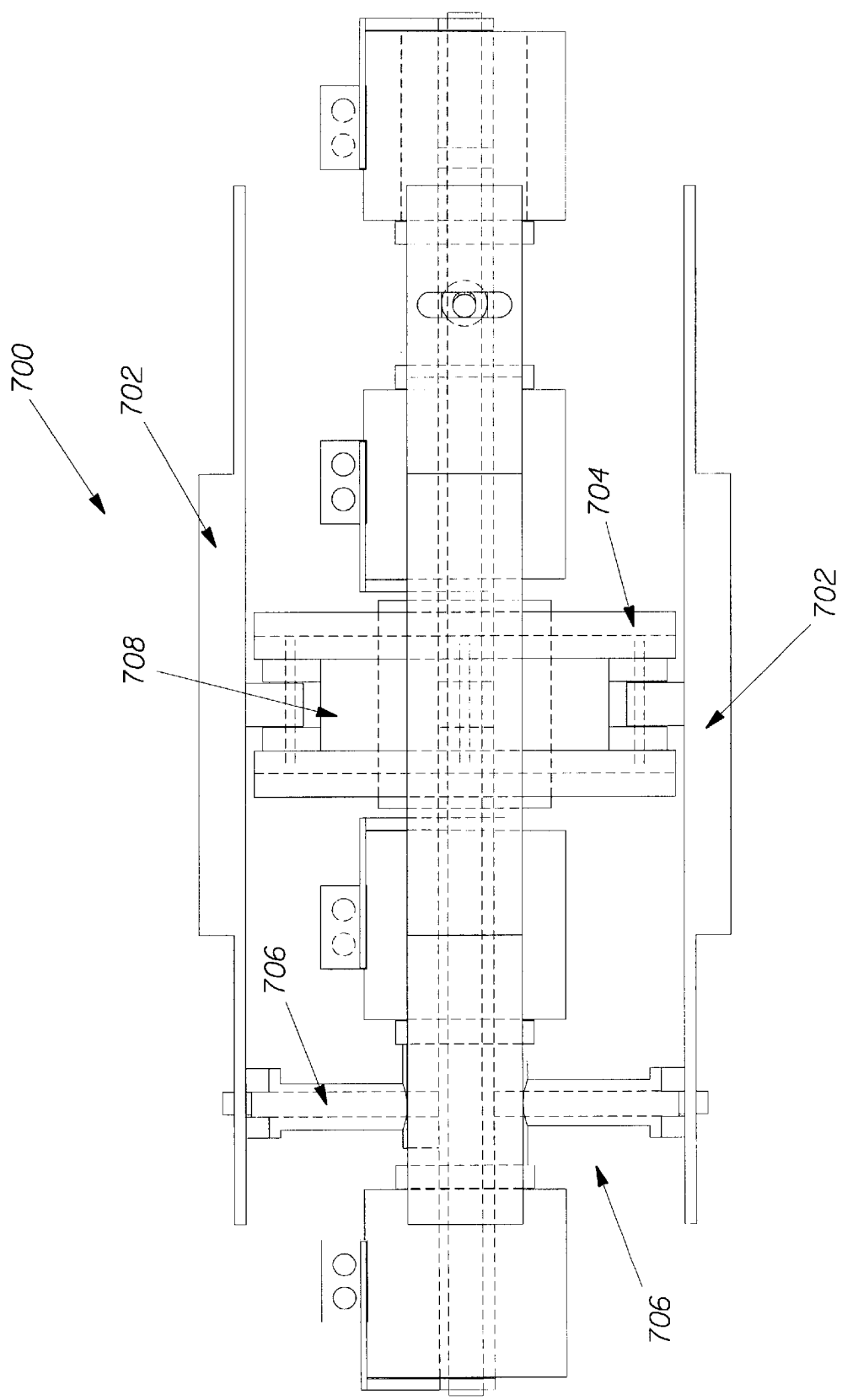
FIG. 21 representatively shows a plan view of the embodiment shown in FIG. 20.
Figure 22:
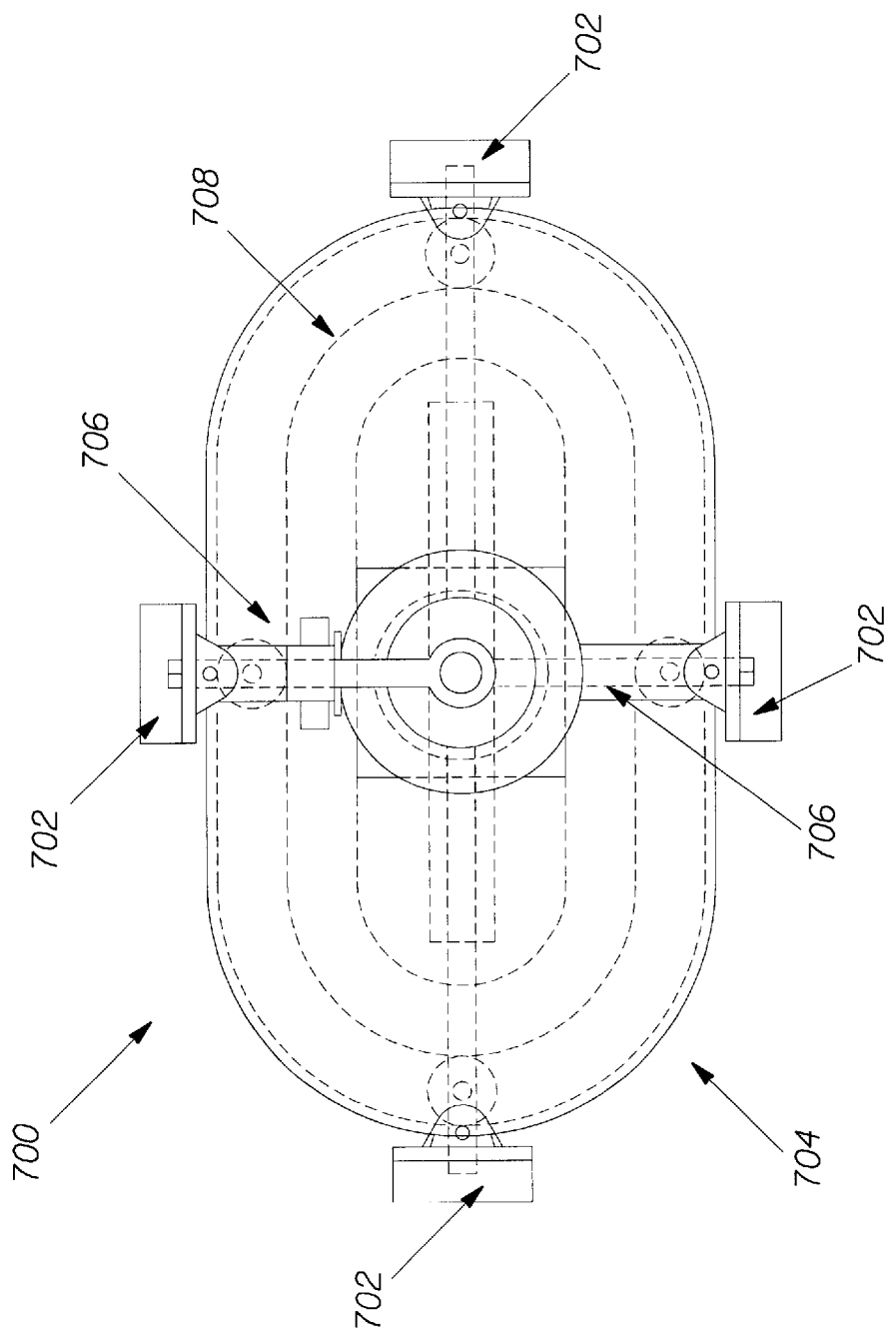
FIG. 22 representatively shows a side view of the embodiment shown in FIGS. 20 and 21.
Figure 23:
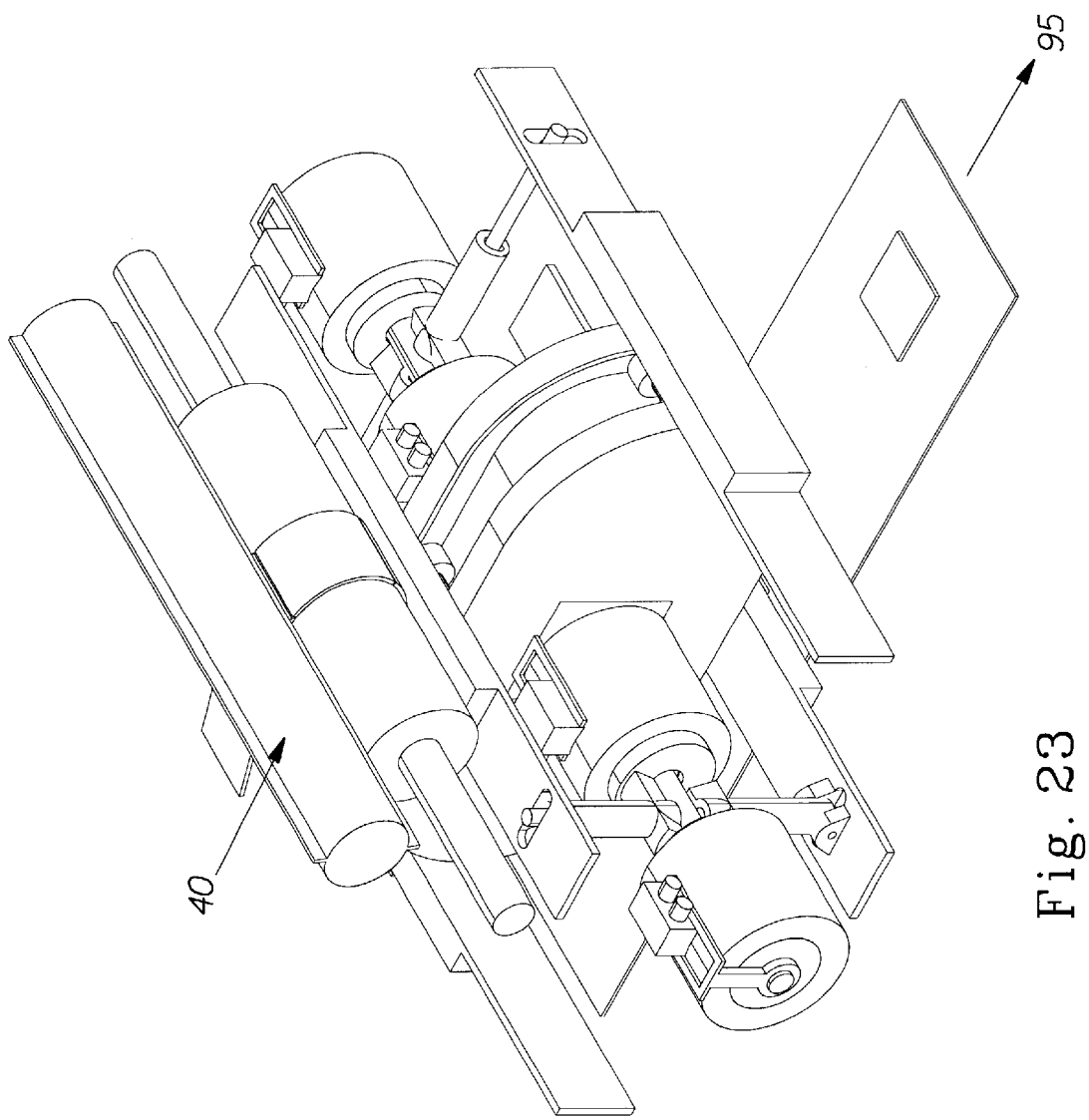
FIG. 23 representatively shows an isometric view of the embodiment shown in FIGS. 20–22 including a cutting device as viewed from downstream.
Figure 24:
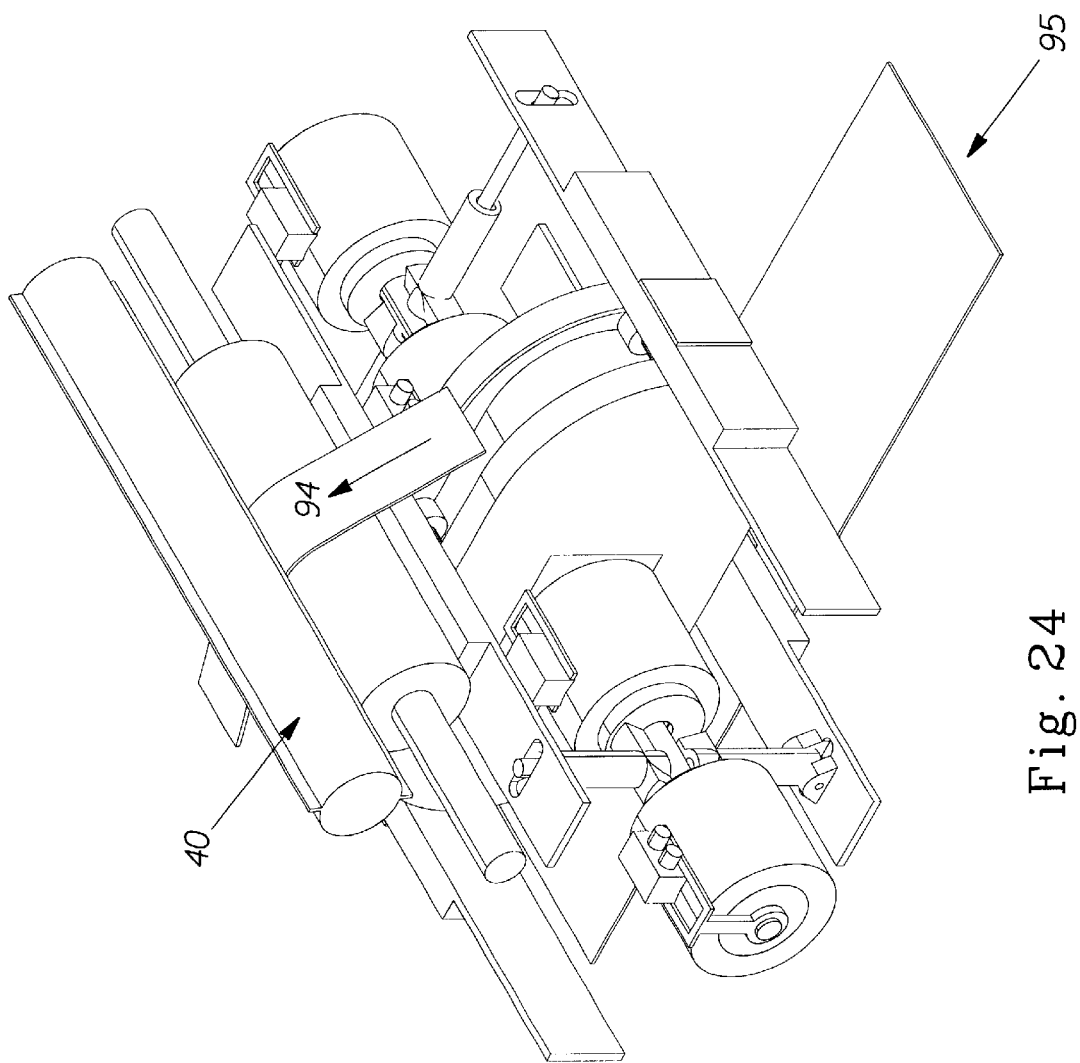
FIG. 24 representatively shows an isometric view of the embodiment shown in FIGS. 20–22 including a cutting device as viewed from upstream.
Figure 25:
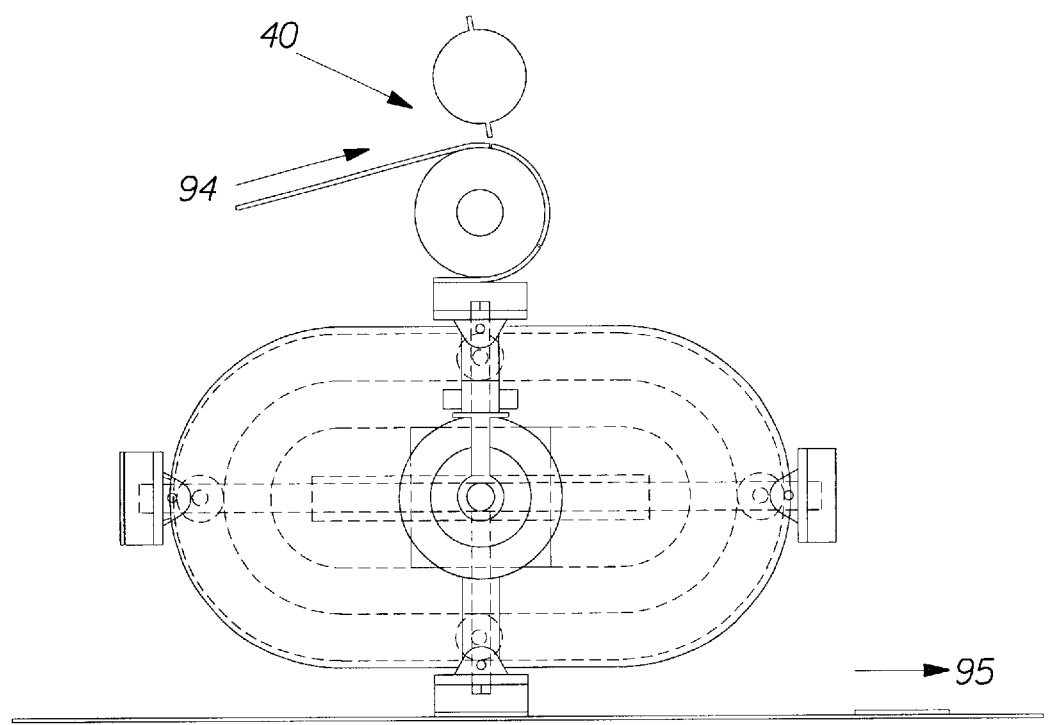
FIG. 25 representatively shows a side view of the embodiment shown in FIGS. 23–24.

FIGS. 20–22 illustrate another embodiment of an apparatus 700 wherein the transferring devices 702 are movable in an orbital path 704 rather than a circular path as described in the apparatus 500 of FIGS. 10–12. The orbital path 704 of the transferring devices 702 is provided via extensible connections 706 in combination with a certain cam profile 708 of the orbital path 704. The motors of apparatus 700 can be any suitable motor described above. FIGS. 23–25 illustrate the above embodiment including the cutting device 40 as previously shown and described above.

Figure 26:
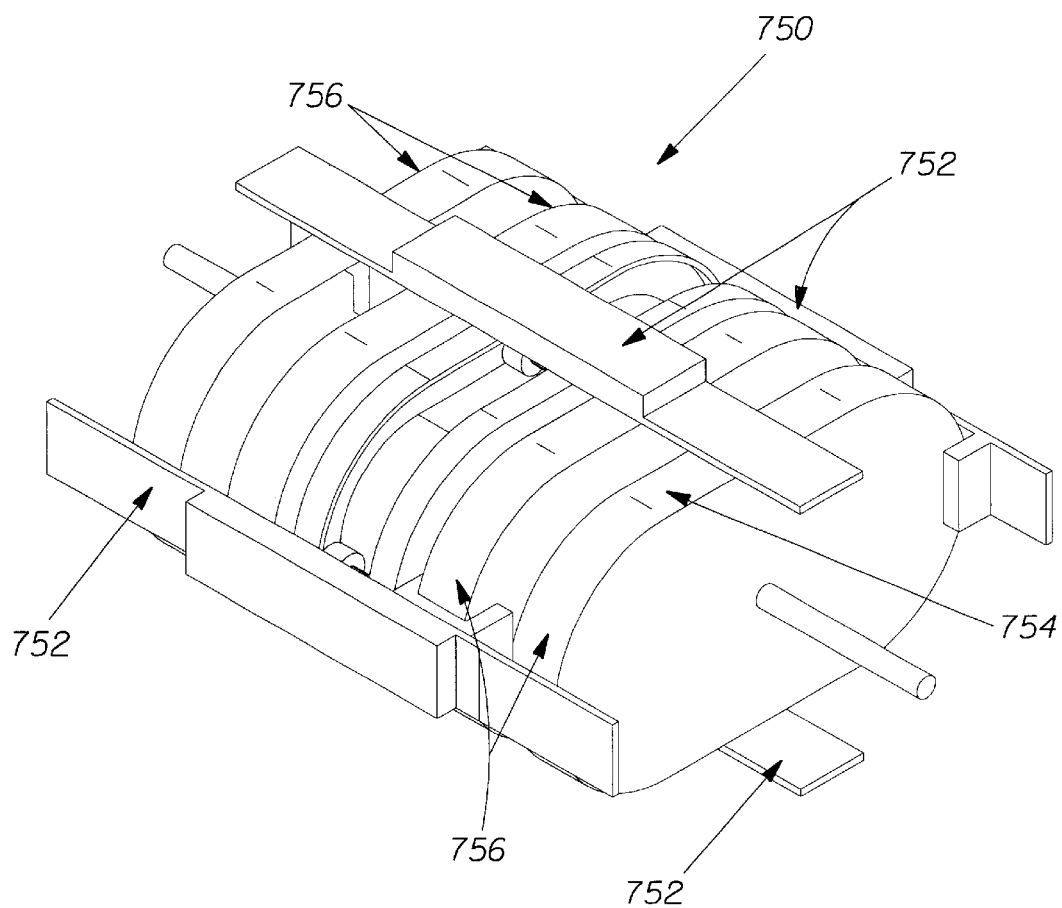
FIG. 26 representatively shows an isometric view of another embodiment of the present invention including a series of motors aligned with a common central axis and wherein each of the motors has at least one stationary planetary track rail and a movable rider.

FIG. 26 illustrates another embodiment of an apparatus 750 wherein the transferring devices 752 are movable in an orbital path 754 provided by the shape of the stationary track 756 of the programmable linear motor.

Figure 27:
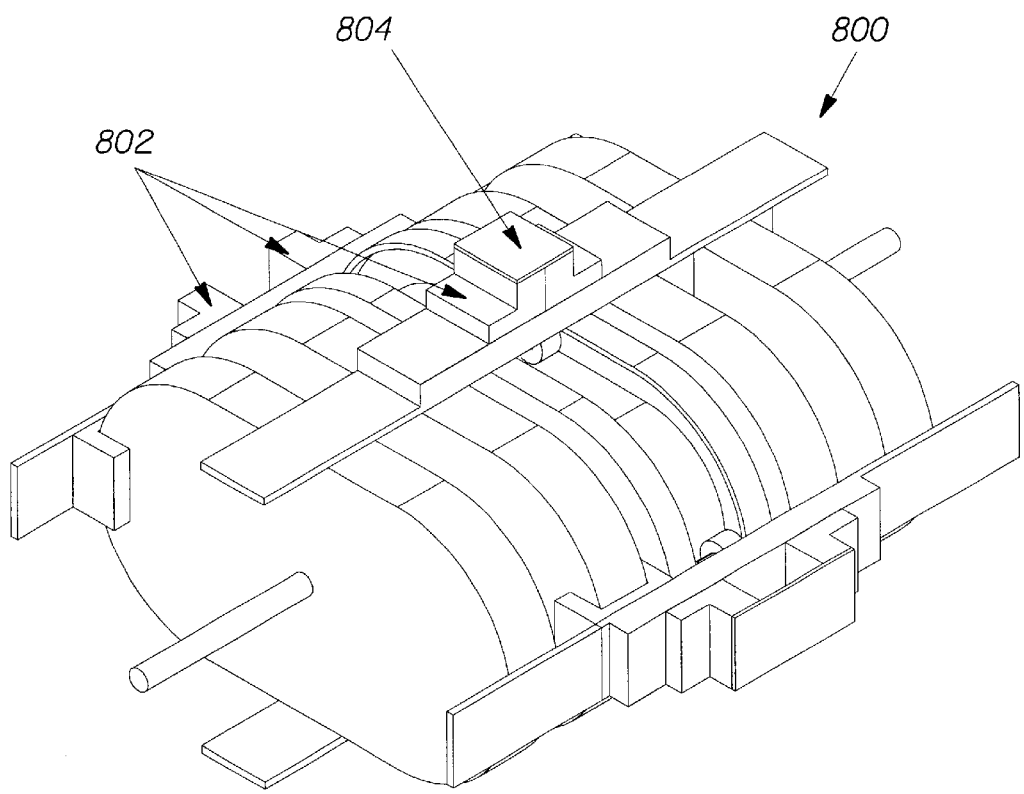
FIG. 27 representatively shows an isometric view of another embodiment of the present invention including a stretching device.
Figure 28:
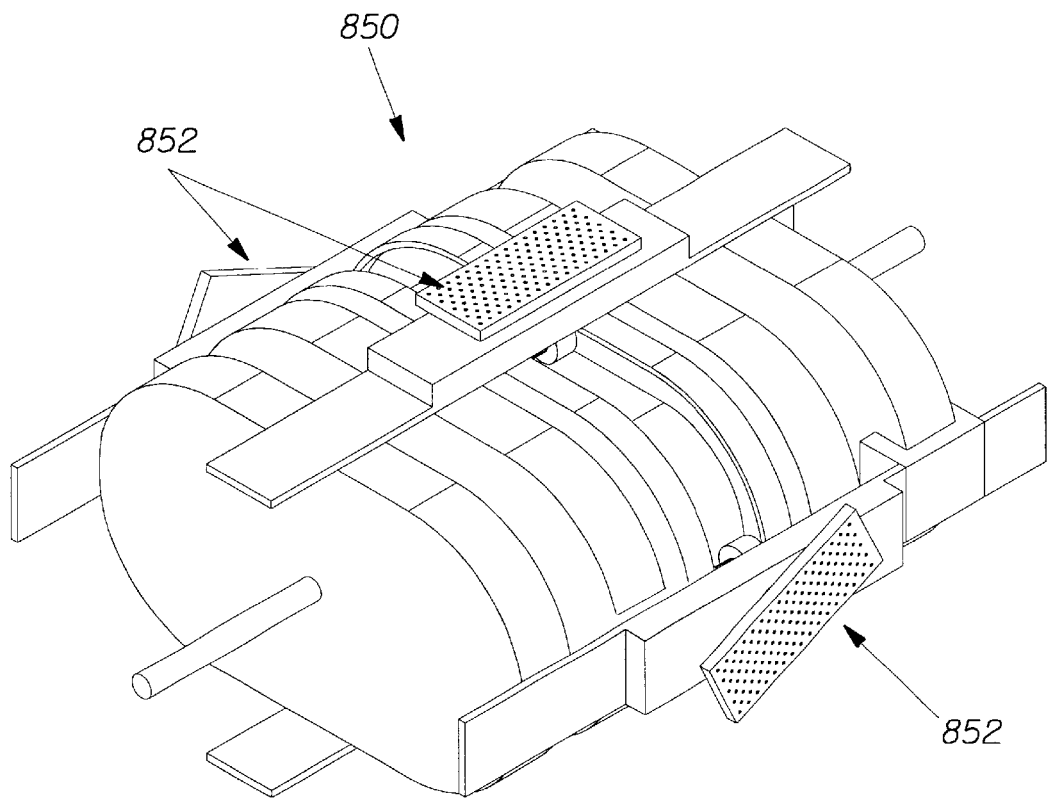
FIG. 28 representatively shows an isometric view of another embodiment of the present invention including a rotating device.

Other alternative additional processes can include operations associated with modifying the physical dimensions, the material properties, and/or the orientation of the discrete parts in relation to the substrate to which it will be attached. Specifically, such operations can include stretching, activation, rotation and the like by any means known to those skilled in the art. For example, FIG. 27 illustrates another embodiment of the apparatus 800 of the present invention including a stretching device 802 for stretching the discrete part 804 before transferring said parts to the substrate. Further, FIG. 28 illustrates another embodiment of the apparatus 850 of the present invention including a rotating device 852 for rotating discrete parts before transferring said parts to the substrate.

Further, certain applications can benefit from having a flexible pitch capability. Typical examples of pitched systems include knife rolls, printing rolls, bonding rolls and the like, as well as the discrete parts transferring applications described thereinabove. The pitch of a system such as a knife roll can be typically changed by adding additional tooling on a roll (e.g., the number of knives on a roll determines the number of pitches per a revolution of a roll), however such approach is not convenient for a rapid change. Other alternatives can include varying the rotational speed of the roll, adding or subtracting spacer plates underneath the tooling to change radial distance from the axis of rotation, or operating the tooling at the appropriate cycle rate but a different surface speed from the substrate it is interacting with. The embodiments of the apparatus of the present invention described thereinabove can offer the benefit of matched speed interactions with the substrate at a desired cycle rate and without a need for physically modifying the system when changing from pitch length to pitch length, even if the pitch length varies either intentionally or unintentionally from product to product during continuous operation.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. An apparatus for receiving parts traveling at a first speed through a receiving zone and applying the parts to a carrier traveling at a second speed through an application zone, the apparatus comprising:

at least two independent programmable motors; and at least two transferring devices for receiving the parts in the receiving zone and applying the parts in the application zone, at least one of the transferring devices being coupled to each of the programmable motors for moving the transferring devices in an orbital path, wherein the programmable motors and the transferring devices are aligned in relation to a common axis, and wherein the programmable motors maintain the transferring devices at first surface speeds in the receiving zone as the transferring devices pick up the parts and maintain the transferring devices at second surface speeds in the application zone as the transferring devices apply the parts to the carrier.

2. The apparatus as defined in claim 1 wherein at least one of the programmable motors is selected from the group consisting of a motor having a hollow rotatable shaft, a linear motor having a stationary track rail, a motor having a rotatable outer rotor and a stationary inner stator, and a motor having a rotor rotatable around a stationary component of a motor.

3. The apparatus as defined in claim 2 wherein at least one of the programmable motors is coupled to at least one of the transferring devices via a transmitting mechanism for moving the at least one of the transferring devices.

4. The apparatus as defined in claim 3 wherein the transmitting mechanism is a rigid connection or an extensible connection.

5. The apparatus as defined in claim 2 wherein the stationary track rail of the linear motor includes a plurality of armature windings therein or a magnetic material therein.

6. The apparatus as defined in claim 5 wherein the linear motor includes at least one rider movable on the stationary track rail.

7. The apparatus as defined in claim 1 wherein the programmable motors are located on a stationary central shaft coaxially with the common axis.

8. The apparatus as defined in claim 1 wherein the first and second surface speeds of the transferring devices are substantially constant.

9. The apparatus as defined in claim 1 wherein the first and second surface speeds of the transferring devices are variable.

10. The apparatus as defined in claim 1 wherein either the first surface speeds of the transferring devices or the second surface speeds of the transferring devices are variable.

11. The apparatus as defined in claim 1 wherein the first surface speeds of the transferring devices are substantially equal to the first speed of the parts in the receiving zone and the second surface speeds of the transferring devices are substantially equal to the second speed of the carrier in the application zone.

12. The apparatus as defined in claim 1 wherein at least one of the transferring devices comprises at least one shell segment having an outer surface, the shell segment is movable along the orbital path that passes through the receiving zone and the application zone during movement of the at least one of the transferring devices, the shell segment collects at least one of the parts in the receiving zone and holds the at least one of the parts against the outer surface utilizing a vacuum, electrostatics, or a coefficient of friction before applying the at least one of the parts to the carrier in the application zone.

13. The apparatus as defined in claim 12 wherein the outer surface of the shell segment is an arcuate surface or a flat surface.

14. The apparatus of claim 1 wherein the orbital path forms a circle or any trajectory including one or more curvilinear or rectilinear sections.

15. The apparatus as defined in claim 1 further comprising an applicator for performing a secondary process on the parts between the receiving zone and the application zone.

16. The apparatus as defined in claim 1 further comprising a cutting device wherein a continuous web of material is cut into parts at the receiving zone.

17. The apparatus as defined in claim 1 wherein the carrier comprises a web substrate, a belt or a drum.

* * * * *

UNITED STATES PATENT AND TRADEMARK OFFICE
CERTIFICATE OF CORRECTION

PATENT NO.    : 6,705,453 B2
DATED         : March 16, 2004
INVENTOR(S)   : Blumenthal et al.

It is certified that error appears in the above-identified patent and that said Letters Patent is hereby corrected as shown below:

Column 9,
Line 2, after "supply", delete "," and insert therefor -- . --.
Line 30, delete "maybe" and insert therefor -- may be --.

Column 10,
Line 67, delete "par" and insert therefor -- part --.

Column 13,
Line 39, delete "devise" and insert therefor -- device --.

Column 14,
Line 17, after "part", insert therefor -- . --.

Column 15,
Line 9, delete "Kolhmorgen" and insert therefore -- Kollmorgen --.

Signed and Sealed this

Twenty-second Day of March, 2005

JON W. DUDAS
*Director of the United States Patent and Trademark Office*

(12) EX PARTE REEXAMINATION CERTIFICATE (8217th)
United States Patent
Blumenthal et al.

(10) Number: US 6,705,453 C1
(45) Certificate Issued: May 10, 2011

(54) METHOD AND APPARATUS UTILIZING SERVO MOTORS FOR PLACING PARTS ONTO A MOVING WEB

(75) Inventors: Jeffrey H. Blumenthal, Batavia, OH (US); Michael J. Lamping, Cincinnati, OH (US)

(73) Assignee: The Procter & Gamble Company, Cincinnati, OH (US)

Reexamination Request:
No. 90/010,869, Mar. 25, 2010

Reexamination Certificate for:
Patent No.: 6,705,453
Issued: Mar. 16, 2004
Appl. No.: 09/897,822
Filed: Jun. 29, 2001

Certificate of Correction issued Mar. 22, 2005.

Related U.S. Application Data

(63) Continuation-in-part of application No. 09/620,867, filed on Jul. 21, 2000, now Pat. No. 6,450,321.

(51) Int. Cl.
*B65G 47/32* (2006.01)

(52) U.S. Cl. ........... 198/471.1; 156/520; 156/521; 156/552; 156/568; 198/408; 198/459.8; 198/460.1; 198/461.2; 198/472.1

(58) Field of Classification Search ............ 198/471
See application file for complete search history.

(56) References Cited

U.S. PATENT DOCUMENTS

| 3,963,557 | A | 6/1976 | Patterson |
| 4,181,555 | A | 1/1980 | Hoffmann |
| 4,297,157 | A | 10/1981 | Van Vliet |
| 4,333,790 | A | 6/1982 | Schaffron |
| 4,429,781 | A | 2/1984 | Holzhauser |
| 4,578,133 | A | 3/1986 | Oshefsky et al. |
| 4,632,721 | A | 12/1986 | Hoffmann et al. |
| 4,726,876 | A | 2/1988 | Tomsovic, Jr. |
| 4,786,046 | A | 11/1988 | Freeman et al. |
| 4,838,982 | A | 6/1989 | Klaeser et al. |
| 4,880,102 | A | 11/1989 | Indrebo |
| 4,960,186 | A | 10/1990 | Honda |
| 5,091,039 | A | 2/1992 | Ujimoto et al. |
| 5,116,452 | A | 5/1992 | Eder |
| 5,149,392 | A | 9/1992 | Plaessmann |
| 5,224,405 | A | 7/1993 | Pohjola |
| 5,235,515 | A | 8/1993 | Ungpiyakul et al. |
| 5,305,653 | A | 4/1994 | Ohtani et al. |
| 5,380,381 | A | 1/1995 | Otruba |
| 5,413,651 | A | 5/1995 | Otruba |

(Continued)

FOREIGN PATENT DOCUMENTS

| AT | 104442 B | 10/1926 |
| CH | 678616 | 10/1991 |
| EP | 0812789 | 12/1997 |
| EP | 1303240 B1 | 8/2008 |
| JP | 62-2959 | 6/1985 |
| JP | 61-42247 | 2/1986 |
| JP | 5-002568 | 1/1993 |
| JP | 5-199689 | 8/1993 |
| JP | 9-509128 | 9/1997 |
| JP | 2000-125538 | 4/2000 |
| JP | 2000-197339 | 7/2000 |
| WO | WO 99/46136 A1 | 9/1999 |
| WO | WO 99/62801 | 12/1999 |
| WO | WO 01/00492 A1 | 1/2001 |
| WO | WO 01/53156 A1 | 7/2001 |
| WO | WO 2005/035414 A1 | 4/2005 |

*Primary Examiner* — William C. Doerrler

(57) ABSTRACT

A method and apparatus for receiving parts traveling at a first speed through a receiving zone and applying the parts to a carrier traveling at a second speed through an application zone. The method and apparatus utilizes transferring devices for transporting the parts between the zones. The transferring devices are coupled to programmble servo motors capable of varying the speed of the transferring devices to accommodate the receiving and application processes.

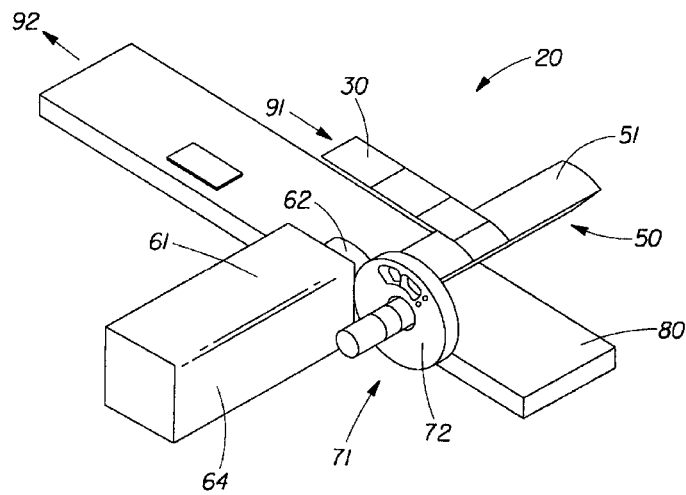

U.S. PATENT DOCUMENTS

| | | |
|---|---|---|
| 5,643,396 A | 7/1997 | Rajala et al. |
| 5,684,344 A | 11/1997 | Takei |
| 5,693,165 A | 12/1997 | Schmitz |
| 5,693,195 A | 12/1997 | Saito et al. |
| 5,709,770 A | 1/1998 | Asghar et al. |
| 5,716,478 A | 2/1998 | Boothe et al. |
| 5,735,996 A | 4/1998 | Asghar et al. |
| 5,766,406 A | 6/1998 | Bohn et al. |
| 5,776,289 A | 7/1998 | Steidinger |
| 5,783,032 A | 7/1998 | O'Callaghan et al. |
| 5,849,143 A | 12/1998 | Ingalls |
| 5,888,343 A | 3/1999 | Olson |
| 5,895,555 A | 4/1999 | Van Den Bergh |
| 5,932,039 A | 8/1999 | Popp et al. |
| 5,965,963 A | 10/1999 | Chitayat |
| 5,994,798 A | 11/1999 | Chitayat |
| 6,022,443 A | 2/2000 | Rajala et al. |
| 6,059,710 A | 5/2000 | Rajala et al. |
| 6,074,333 A | 6/2000 | Rajala et al. |
| 6,086,694 A | 7/2000 | Winter et al. |
| 6,139,004 A | 10/2000 | Couillard et al. |
| 6,149,755 A | 11/2000 | McNichols et al. |
| 6,165,306 A | 12/2000 | Rajala |
| 6,350,070 B1 | 2/2002 | Tasma |
| 6,431,241 B1 | 8/2002 | Gonzalo |
| 6,450,321 B1 | 9/2002 | Blumenthal et al. |
| 6,766,843 B2 | 7/2004 | Hilt et al. |
| 6,811,019 B2 | 11/2004 | Christian et al. |
| 6,814,217 B2 | 11/2004 | Blumenthal et al. |
| 6,820,671 B2 | 11/2004 | Calvert |
| 2003/0079330 A1 | 5/2003 | Stopher et al. | and Jones[2,3]

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 12 are determined to be patentable as amended.

Claims 2-11 and 13-17, dependent on an amended claim, are determined to be patentable.

New claims 18-31 are added and determined to be patentable.

1. An apparatus for receiving parts traveling at a first speed through a receiving zone and applying the parts to a carrier traveling at a second speed through an application zone, the apparatus comprising:
at least two independent programmable motors; and
at least two transferring devices for receiving the parts in the receiving zone and applying the parts in the application zone, at least one of the transferring devices being coupled to each of the programmable motors for moving the transferring devices in an orbital path,
wherein the programmable motors and the transferring devices are aligned in relation to a common axis,
*wherein each of the at least two transferring devices comprises a shell segment having an outer surface,*
*wherein the shell segments of the at least two transferring devices are located between the at least two independent programmable motors,* and
wherein the programmable motors maintain the transferring devices at first surface speeds in the receiving zone as the transferring devices pick up the parts and maintain the transferring devices at second surface speeds in the application zone as the transferring devices apply the parts to the carrier.

12. The apparatus as defined in claim 1 wherein [at least one of the transferring devices comprises] at least one shell segment [having an outer surface, the shell segment] is movable along the orbital path that passes through the receiving zone and the application zone during movement of the at least one of the transferring devices, the shell segment collects at least one of the parts in the receiving zone and holds the at least one of the parts against the outer surface utilizing a vacuum, electrostatics, or a coefficient of friction before applying the at least one of the parts to the carrier in the application zone.

*18. An apparatus for receiving parts traveling at a first speed through a receiving zone and applying the parts to a carrier traveling at a second speed through an application zone, the apparatus comprising:*
*at least two independent programmable motors; and*
*at least two transferring devices for receiving the parts in the receiving zone and applying the parts in the application zone, at least one of the transferring devices being coupled to each of the programmable motors for moving the transferring devices in an orbital path,*
*wherein at least one of the programmable motors is a linear motor having a stationary track rail,*
*wherein the programmable motors and the transferring devices are aligned in relation to a common axis, and*
*wherein the programmable motors maintain the transferring devices at first surface speeds in the receiving zone as the transferring devices pick up the parts and maintain the transferring devices at second surface speeds in the application zone as the transferring devices apply the parts to the carrier.*

*19. The apparatus as defined in claim 18 wherein at least one of the programmable motors is coupled to at least one of the transferring devices via a transmitting mechanism for moving the at least one of the transferring devices.*

*20. The apparatus as defined in claim 19 wherein the transmitting mechanism is a rigid connection or an extensible connection.*

*21. The apparatus as defined in claim 18 wherein the stationary track rail of the linear motor includes a plurality of armature windings therein or a magnetic material therein.*

*22. The apparatus as defined in claim 21 wherein the linear motor includes at least one rider movable on the stationary track rail.*

*23. The apparatus as defined in claim 18 wherein the first and second surface speeds of the transferring devices are substantially constant.*

*24. The apparatus as defined in claim 18 wherein the first and second surface speeds of the transferring devices are variable.*

*25. The apparatus as defined in claim 18 wherein either the first surface speeds of the transferring devices or the second surface speeds of the transferring devices are variable.*

*26. The apparatus as defined in claim 18 wherein the first surface speeds of the transferring devices are substantially equal to the first speed of the parts in the receiving zone and the second surface speeds of the transferring devices are substantially equal to the second speed of the carrier in the application zone.*

*27. The apparatus as defined in claim 18 wherein at least one of the transferring devices comprises at least one shell segment having an outer surface, the shell segment is movable along the orbital path that passes through the receiving zone and the application zone during movement of the at least one of the transferring devices, the shell segment collects at least one of the parts in the receiving zone and holds the at least one of the parts against the outer surface utilizing a vacuum, electrostatics, or a coefficient of friction before applying the at least one of the parts to the carrier in the application zone.*

*28. The apparatus as defined in claim 12 wherein the outer surface of the shell segment is an arcuate surface or a flat surface.*

*29. The apparatus as defined in claim 18 further comprising an applicator for performing a secondary process on the parts between the receiving zone and the application zone.*

*30. The apparatus as defined in claim 18 further comprising a cutting device wherein a continuous web of material is cut into parts at the receiving zone.*

*31. The apparatus as defined in claim 18 wherein the carrier comprises a web substrate, a belt or a drum.*

\* \* \* \* \*